US012696892B2

(12) United States Patent
Anderson et al.

(10) Patent No.: US 12,696,892 B2
(45) Date of Patent: Aug. 4, 2026

(54) PREVENTING DAMAGE BY FARMING MACHINE

(71) Applicant: Deere & Company, Moline, IL (US)

(72) Inventors: Kent Anderson, Signal Mountain, TN (US); Ben Chostner, San Francisco, CA (US); Bryon Majusiak, Incline Village, NV (US); Divya Sharma, Incline Village, NV (US); Lee Redden, Palo Alto, CA (US)

(73) Assignee: Deere & Company, Moline, IL (US)

( * ) Notice: Subject to any disclaimer, the term of this patent is extended or adjusted under 35 U.S.C. 154(b) by 328 days.

(21) Appl. No.: 17/396,193

(22) Filed: Aug. 6, 2021

(65) Prior Publication Data

US 2023/0039092 A1    Feb. 9, 2023

(51) Int. Cl.
*A01M 7/00*        (2006.01)
*A01B 79/00*       (2006.01)
*G01N 33/24*       (2006.01)

(52) U.S. Cl.
CPC ......... *A01M 7/0089* (2013.01); *A01B 79/005* (2013.01); *G01N 33/246* (2013.01); *G01N 33/245* (2024.05)

(58) Field of Classification Search
CPC .......................... A01M 7/0089; A01B 79/005
USPC ...................................... 701/36–50
See application file for complete search history.

(56) References Cited

U.S. PATENT DOCUMENTS

| | | | |
|---|---|---|---|
| 5,751,576 A | 5/1998 | Monson | |
| 5,884,224 A | 3/1999 | Mcnabb et al. | |
| 6,427,781 B1 | 8/2002 | Buhler et al. | |

| | | | | |
|---|---|---|---|---|
| 9,139,998 B1 | 9/2015 | Conner et al. | | |
| 9,658,201 B2 | 5/2017 | Redden et al. | | |
| 10,912,251 B2 | 2/2021 | Pickett et al. | | |
| 11,479,213 B1 | 10/2022 | Kentley-Klay | | |
| 2008/0131202 A1* | 6/2008 | Slater ..................... | E01C 9/086 | |
| | | | 404/36 | |

(Continued)

FOREIGN PATENT DOCUMENTS

| | | | | |
|---|---|---|---|---|
| JP | 2007099110 A | * | 4/2007 | |
| JP | 2016190607 A | * | 11/2016 | |
| WO | WO 2019089853 A1 | | 5/2019 | |

OTHER PUBLICATIONS

Furuya Shimpei—English description of JP-2016190607-A via Espacenet Patent Translate, retrieved Nov. 6, 2025 (Year: 2025).*

(Continued)

*Primary Examiner* — Erin M Piateski
*Assistant Examiner* — Paul Allen
(74) *Attorney, Agent, or Firm* — Fenwick and West LLP

(57)        ABSTRACT

A farming machine moves through a field and performs one or more farming actions (e.g., treating one or more plants) in the field. Portions of the field may include moisture, such as puddles or mud patches. A control system associated with the farming machine may include a traversability model and/or a moisture model to help the farming machine operate in the field with the moisture. In particular, the control system may employ the traversability model to reduce the likelihood of the farming machine attempting to traverse an untraversable portion of the field, and the control system may employ the moisture model to reduce the likelihood of the farming machine performing an action that will damage a portion of the field.

17 Claims, 15 Drawing Sheets

(56) References Cited

U.S. PATENT DOCUMENTS

| | | | |
|---|---|---|---|
| 2012/0237083 A1 | 9/2012 | Lange et al. | |
| 2012/0323452 A1* | 12/2012 | Green | A01B 79/005 |
| | | | 701/50 |
| 2014/0236431 A1* | 8/2014 | Hendrickson | A01B 69/007 |
| | | | 701/50 |
| 2015/0338848 A1 | 11/2015 | Kumar et al. | |
| 2016/0108606 A1 | 4/2016 | Strutynsky | |
| 2017/0101103 A1* | 4/2017 | Foster | A01B 63/11 |
| 2018/0025560 A1 | 1/2018 | Matsuzaki et al. | |
| 2018/0050704 A1 | 2/2018 | Tascione et al. | |
| 2018/0070527 A1 | 3/2018 | Richt | |
| 2018/0092295 A1 | 4/2018 | Sugumaran et al. | |
| 2018/0257657 A1 | 9/2018 | Blank et al. | |
| 2018/0268532 A1* | 9/2018 | Wang | B60C 11/246 |
| 2018/0271015 A1 | 9/2018 | Redden et al. | |
| 2019/0129435 A1 | 5/2019 | Madsen et al. | |
| 2019/0150357 A1* | 5/2019 | Wu | H04N 23/51 |
| 2019/0217864 A1 | 7/2019 | Kusukame et al. | |
| 2019/0362146 A1 | 11/2019 | Polzounov et al. | |
| 2020/0029490 A1 | 1/2020 | Bertucci et al. | |
| 2020/0093054 A1* | 3/2020 | Aesaert | G01N 33/24 |
| 2020/0107490 A1 | 4/2020 | Zemenchik | |
| 2020/0114843 A1 | 4/2020 | Foster et al. | |
| 2020/0128734 A1* | 4/2020 | Brammeier | A01D 41/1275 |
| 2020/0193589 A1 | 6/2020 | Peshlov et al. | |
| 2020/0236834 A1 | 7/2020 | Balani et al. | |
| 2020/0236836 A1 | 7/2020 | Barrick et al. | |
| 2020/0344939 A1 | 11/2020 | Sporrer et al. | |
| 2021/0029865 A1 | 2/2021 | Smith et al. | |
| 2021/0120730 A1* | 4/2021 | Anderson | G06Q 10/047 |
| 2021/0149406 A1 | 5/2021 | Javault et al. | |
| 2021/0173399 A1* | 6/2021 | Richard | B60W 50/14 |
| 2021/0191409 A1 | 6/2021 | Ready-Campbell et al. | |
| 2021/0192294 A1 | 6/2021 | Stanhope et al. | |
| 2021/0251128 A1 | 8/2021 | Rupp et al. | |
| 2021/0321568 A1 | 10/2021 | Garton et al. | |
| 2021/0404812 A1* | 12/2021 | Yuasa | A01B 37/00 |
| 2022/0026921 A1 | 1/2022 | Halder | |
| 2022/0117215 A1 | 4/2022 | Sibley et al. | |
| 2022/0183209 A1 | 6/2022 | Scott-Robinson et al. | |
| 2022/0269282 A1 | 8/2022 | Ascherl et al. | |
| 2022/0327335 A1* | 10/2022 | Thopalli | G06Q 10/08 |
| 2022/0406104 A1 | 12/2022 | Maeder et al. | |
| 2023/0039092 A1 | 2/2023 | Anderson et al. | |
| 2023/0040430 A1 | 2/2023 | Redden et al. | |
| 2023/0121070 A1* | 4/2023 | Kanai | G05D 1/0289 |
| | | | 701/23 |
| 2023/0255137 A1 | 8/2023 | Mcmahan et al. | |
| 2023/0256972 A1* | 8/2023 | Roy | B60C 23/20 |
| | | | 73/146 |
| 2024/0026655 A1 | 1/2024 | Stander et al. | |

OTHER PUBLICATIONS

Obara Masaaki—English description of JP-2007099110-A via Espacenet Patent Translate, Mar. 3, 2026. (Year: 2026).*
PCT International Search Report and Written Opinion, PCT Application No. PCT/US2022/39462, Feb. 7, 2023, 14 pages.
PCT International Search Report and Written Opinion, PCT Application No. PCT/US22/39085, Oct. 31, 2022, 15 pages.
Rankin, A.L. et al., "Daytime Water Detection by Fusing Multiple Cues for Autonomous Off-Road Navigation," 24th Army Science Conference, Nov. 2004, pp. 1-8.
United States Office Action, U.S. Appl. No. 17/396,170, filed Aug. 25, 2023, 15 pages.
Extended European Search Report and Written Opinion issued in European Patent Application No. 22853778.3 dated Jan. 16, 2025, in 10 pages.
European Patent Office, Extended European Search Report, European Patent Application No. 22853778.3, Jan. 16, 2025, 10 pages.
Extended European Search Report and Written Opinion issued in European Patent Application No. 22853921.9 dated May 21, 2025, in 11 pages.
PCT Invitation to Pay Additional Fees, PCT Application No. PCT/US22/39462, Nov. 23, 2022, 2 pages.
United States Office Action, U.S. Appl. No. 17/881,436, filed Nov. 25, 2024, 12 pages.

* cited by examiner

FIG. 2

Method
500

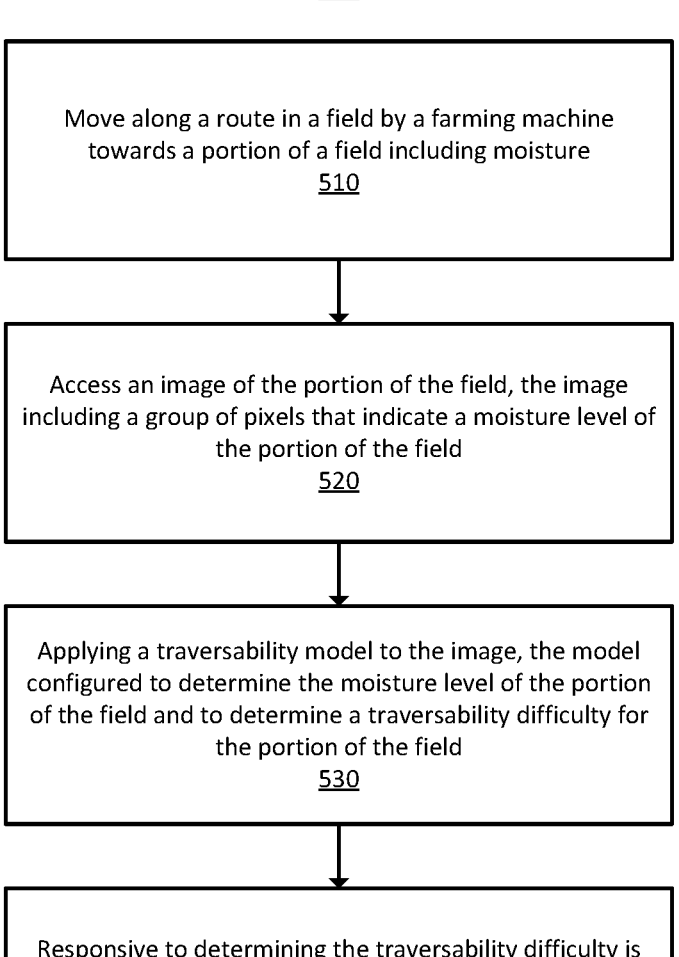

Move along a route in a field by a farming machine
towards a portion of a field including moisture
510

Access an image of the portion of the field, the image
including a group of pixels that indicate a moisture level of
the portion of the field
520

Applying a traversability model to the image, the model
configured to determine the moisture level of the portion
of the field and to determine a traversability difficulty for
the portion of the field
530

Responsive to determining the traversability difficulty is
above a traversability capability of the farming machine,
perform a farming action in the field
540

FIG. 5

Field 605

Mud Patch 610

Water 615

Method
700

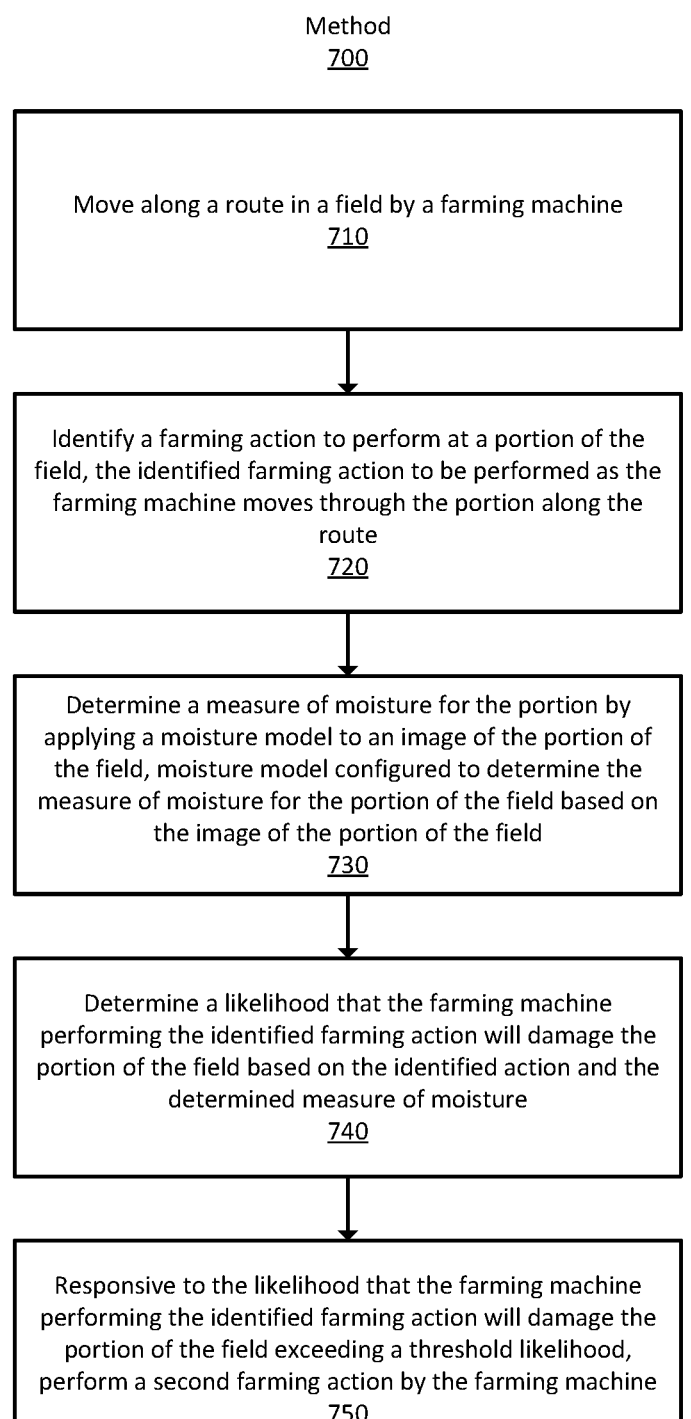

Move along a route in a field by a farming machine
710

Identify a farming action to perform at a portion of the field, the identified farming action to be performed as the farming machine moves through the portion along the route
720

Determine a measure of moisture for the portion by applying a moisture model to an image of the portion of the field, moisture model configured to determine the measure of moisture for the portion of the field based on the image of the portion of the field
730

Determine a likelihood that the farming machine performing the identified farming action will damage the portion of the field based on the identified action and the determined measure of moisture
740

Responsive to the likelihood that the farming machine performing the identified farming action will damage the portion of the field exceeding a threshold likelihood, perform a second farming action by the farming machine
750

FIG. 7

Accessed Image
800

Convolutional
Layer
810

$W_1$

Intermediate
Encoder Layers
820

Moisture Model
805

$W_2$

Identification Layer
830

$W_3$

Intermediate
Decoder Layers
840

$W_4$

Output Layer
850

Measure of
Moisture
860

PREVENTING DAMAGE BY FARMING MACHINE

BACKGROUND

Field of Disclosure

This disclosure relates to operating a farming machine in a field with moisture, and, more specifically, to preventing the farming machine from attempting to traverse untraversable areas in the field or from damaging the field.

Description of the Related Art

Operating a farming machine in a field with moisture, such as puddles and mud, can pose difficulties for an operator of the farming machine. A field with moisture can increase the likelihood of the farming machine becoming immobilized (e.g., getting stuck) in the field or damaging the field (e.g., damaging rows or forming a water run-off channel). An immobilized farming machine can be difficult to free, can delay field operations, and can damage the field, which may reduce the crop output. Preventing the farming machine from becoming immobilized or damaging the field often requires knowledge of the capabilities of the farming machine and of the amount of moisture in the field. This knowledge may be difficult to ascertain or may require the operator to have extensive working experience with the farming machine and the field.

SUMMARY

A farming machine moves through a field and performs one or more farming actions (e.g., treating one or more plants) in the field. Portions of the field may include moisture, such as puddles or mud patches. A control system associated with the farming machine may include a traversability model and/or a moisture model to help the farming machine operate in the field.

To reduce the likelihood of the farming machine becoming immobilized in a field portion (e.g., due to the moisture in the field portion), the control system applies the traversability model to an image of the field portion (the image may be captured by an image sensor of the farming machine). By analyzing pixels in the image, the traversability model determines a moisture level of the field portion and determines a traversability difficulty of the field portion using the moisture level. The traversability difficulty quantifies a level of difficulty for a vehicle to move through the portion of the field. If the traversability difficulty is above a traversability capability of the farming machine, the farming machine performs a farming action, such as modifying the farming machine's route so that it does not move through the portion of the field.

To reduce the likelihood of the farming machine damaging the portion of the field (e.g., due to the moisture in the field portion), the control system applies the moisture model to the image of the field portion. The moisture model determines a measure of moisture for the field portion of the field using the image. Based on the determined measure of moisture, the control system determines a likelihood that the farming machine performing the farming action will damage the portion of the field. If the likelihood is above a threshold likelihood, the farming machine performs another farming action, where the likelihood that the farming machine performing the other farming action will damage the portion of the field is below the threshold likelihood.

BRIEF DESCRIPTION OF DRAWINGS

FIG. 2 illustrates a cross-sectional view of a farming machine including a sensor configured to capture an image of one or more plants, in accordance with an example embodiment.

FIG. 5 illustrates a method for operating in a field with moisture by a farming machine, in accordance with an example embodiment.

FIG. 7 illustrates another method for operating in a field with moisture by a farming machine, in accordance with an example embodiment.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

I. Introduction

A farming machine includes one or more sensors capturing information about the surrounding environment as the farming machine moves through a field. The surrounding environment can include various objects (i.e., plants, ground, obstructions, etc.) used to determine farming actions (e.g., performing a treatment action, modifying a treatment parameter, modifying an operational parameter, and modifying a sensor parameter, etc.) for the farming machine to operate in the field.

The farming machine includes a control system that processes the information obtained by the sensors to generate corresponding farming actions. For example, the control system processes information to identify plants and other objects to generate corresponding treatment actions. There are many examples of a farming machine processing visual information obtained by an image sensor coupled to the farming machine to identify and treat plants and identify and avoid obstructions. For example, similar to the farming machine as described in U.S. patent application Ser. No. 16/126,842 titled "Semantic Segmentation to Identify and Treat Plants in a Field and Verify the Plant Treatments," filed on Sep. 10, 2018, which is hereby incorporated by reference in its entirety.

II. Farming Machine

Figure 1A:
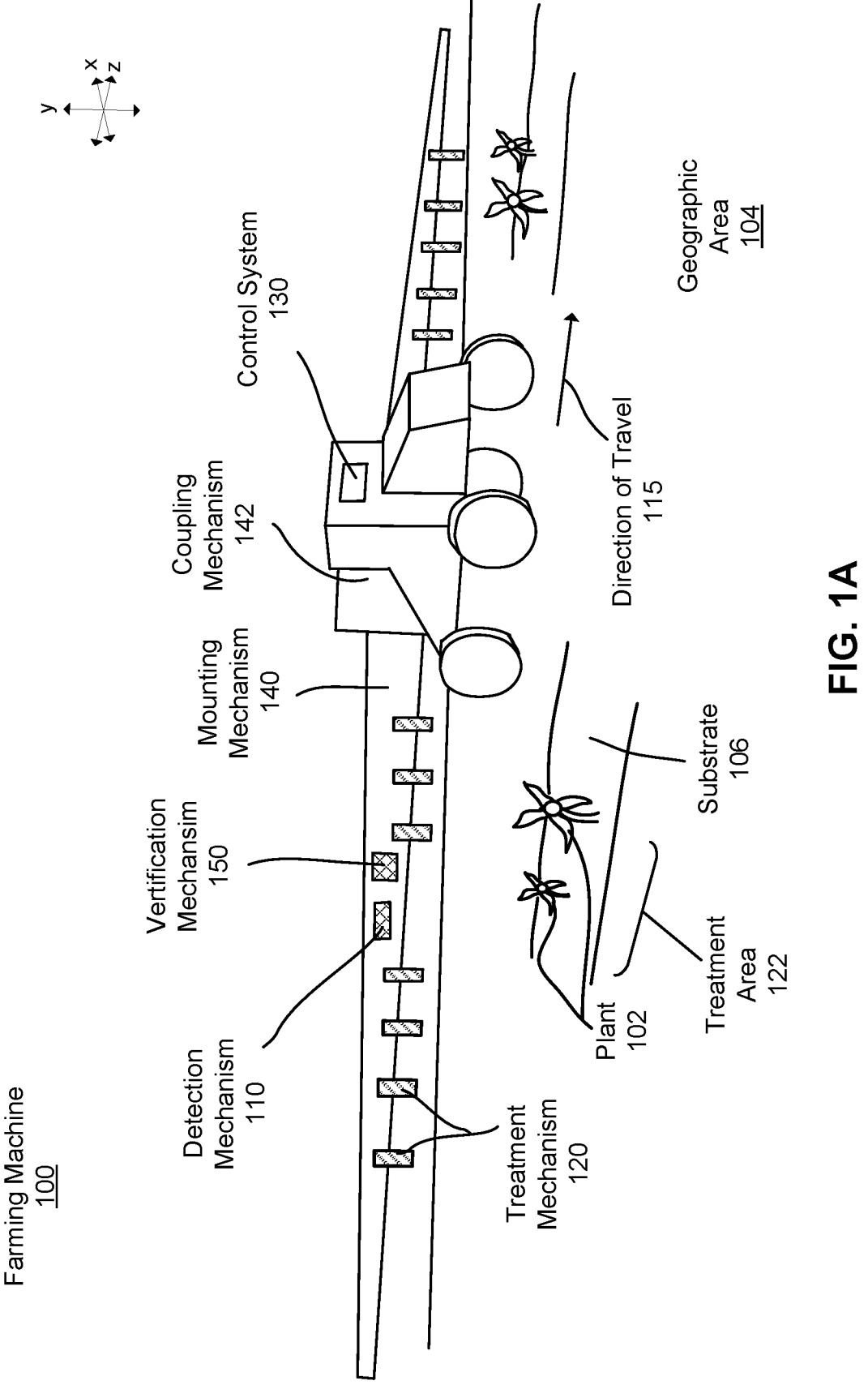
FIG. 1A illustrates an isometric view of a farming machine, in accordance with an example embodiment.
Figure 1B:
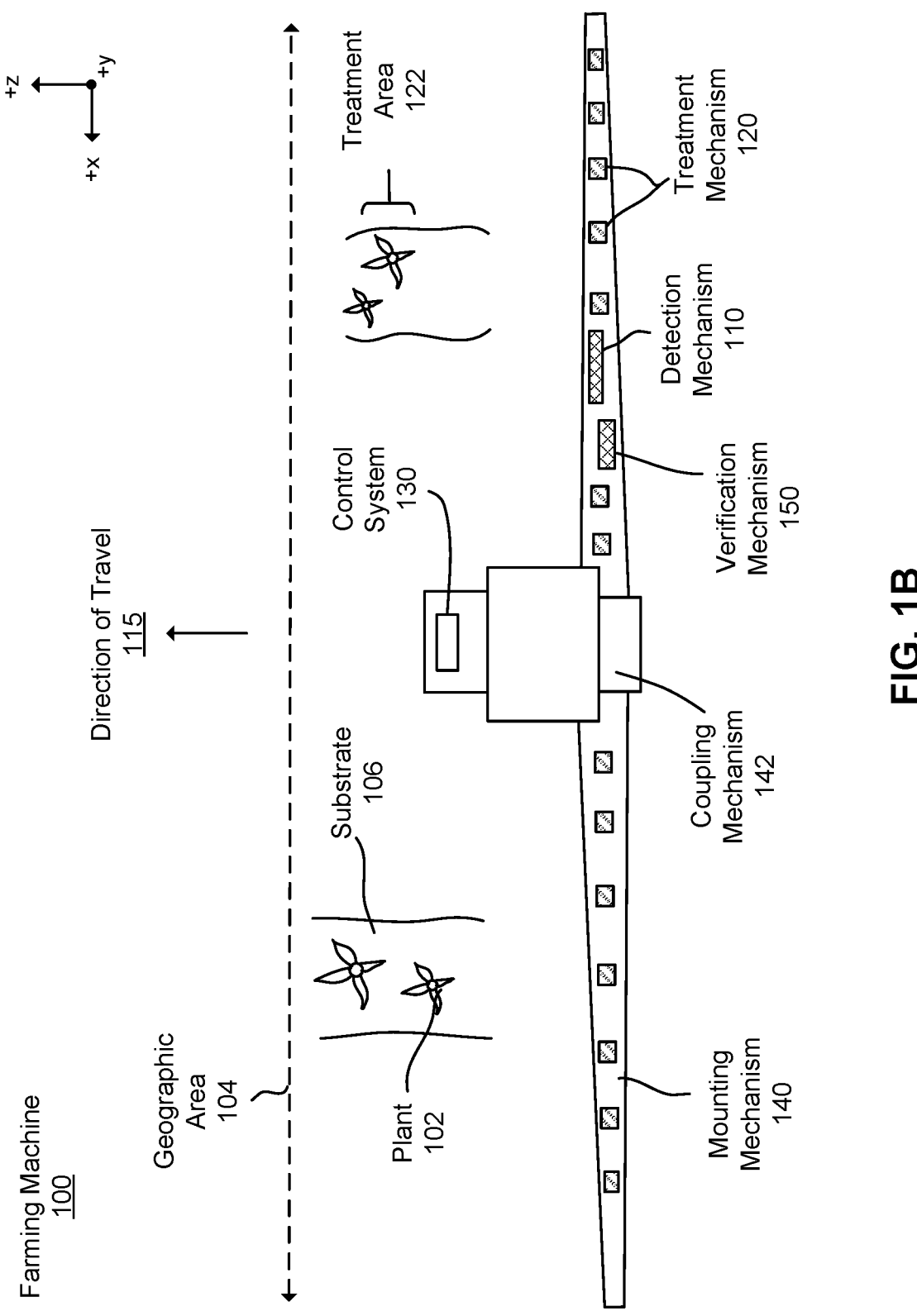
FIG. 1B illustrates a top view of a farming machine, in accordance with the example embodiment.
Figure 1C:
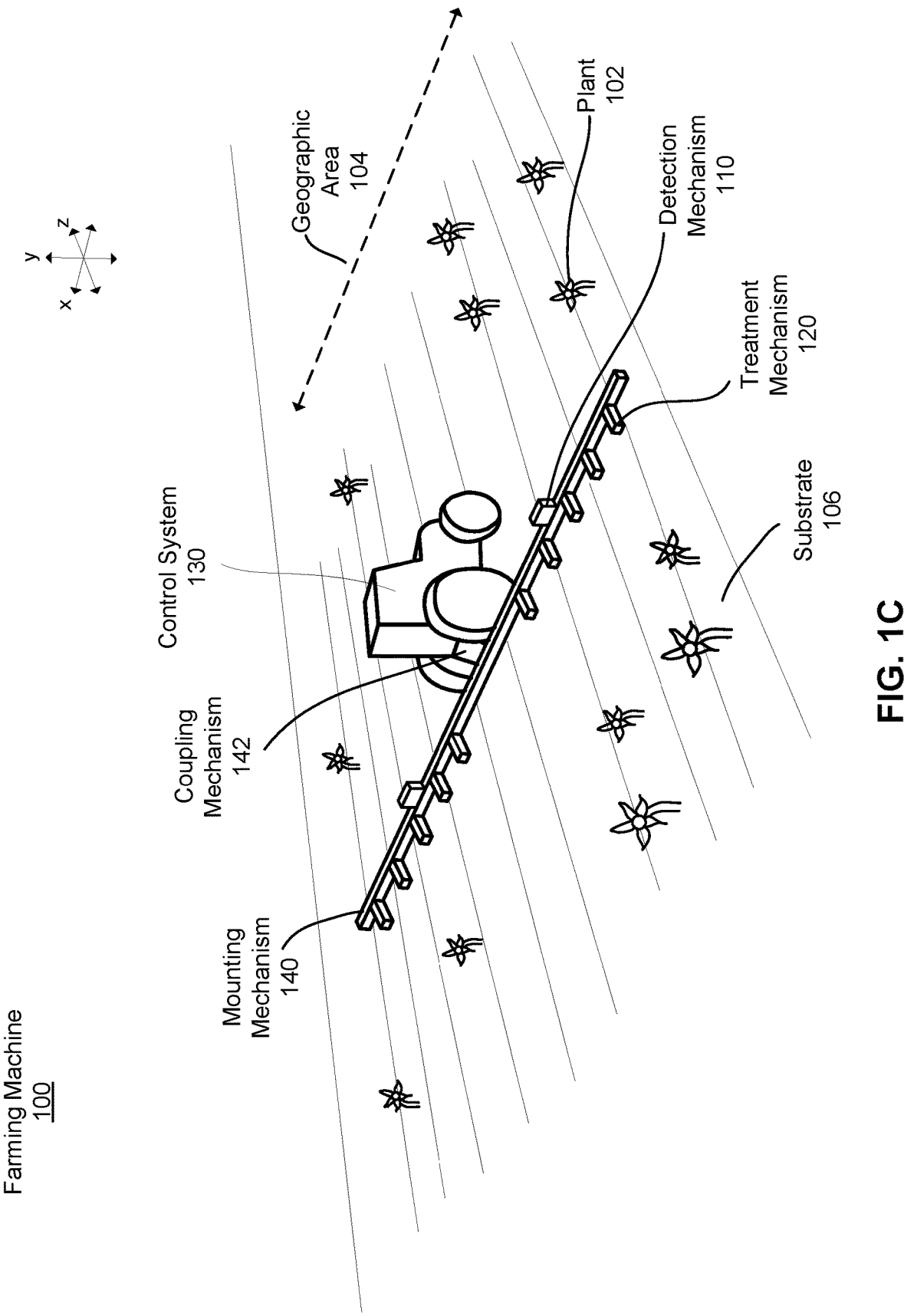
FIG. 1C illustrates an isometric view of a farming machine, in accordance with a second example embodiment.

A farming machine is a vehicle that operates in a field. The farming machine may have a variety of configurations, some of which are described in greater detail below. For example, FIG. 1A is an isometric view of a farming machine and FIG. 1B is a top view of the farming machine of FIG. 1A. FIG. 1C is a second embodiment of a farming machine. Other embodiments of a farming machine are also possible. The farming machine 100, illustrated in FIGS. 1A-1C, includes a detection mechanism 110, a treatment mechanism 120, and a control system 130. The farming machine 100 can additionally include a mounting mechanism 140, a verification mechanism 150, a power source, digital memory, communication apparatus, or any other suitable component. The farming machine 100 can include additional or fewer components than described herein. Furthermore, the components of the farming machine 100 can have different or additional functions than described below.

The farming machine 100 may perform treatment actions in the field. A treatment actions relates to soil preparation (e.g., tilling), planting, regulating plant growth, or harvesting. For example, the farming machine 100 may function to apply a treatment to one or more plants 102 within a geographic area 104. Often, treatments function to regulate plant growth. The treatment is directly applied to a single plant 102 (e.g., hygroscopic material), but can alternatively be directly applied to multiple plants, indirectly applied to one or more plants, applied to the environment associated with the plant (e.g., soil, atmosphere, or other suitable portion of the plant environment adjacent to or connected by an environmental factor, such as wind), or otherwise applied to the plants. Treatments that can be applied include necrosing the plant, necrosing a portion of the plant (e.g., pruning), regulating plant growth, or any other suitable plant treatment. Necrosing the plant can include dislodging the plant from the supporting substrate 106, incinerating a portion of the plant, applying a treatment concentration of working fluid (e.g., fertilizer, hormone, water, etc.) to the plant, or treating the plant in any other suitable manner. Regulating plant growth can include promoting plant growth, promoting growth of a plant portion, hindering (e.g., retarding) plant or plant portion growth, or otherwise controlling plant growth. Examples of regulating plant growth includes applying growth hormone to the plant, applying fertilizer to the plant or substrate, applying a disease treatment or insect treatment to the plant, electrically stimulating the plant, watering the plant, pruning the plant, or otherwise treating the plant. Plant growth can additionally be regulated by pruning, necrosing, or otherwise treating the plants adjacent to the plant.

The plants 102 can be crops but can alternatively be weeds or any other suitable plant. The crop may be cotton, but can alternatively be lettuce, soybeans, rice, carrots, tomatoes, corn, broccoli, cabbage, potatoes, wheat or any other suitable commercial crop. The plant field in which the system is used is an outdoor plant field, but can alternatively be plants within a greenhouse, a laboratory, a grow house, a set of containers, a machine, or any other suitable environment. The plants are grown in one or more plant rows (e.g., plant beds), wherein the plant rows are parallel, but can alternatively be grown in a set of plant pots, wherein the plant pots can be ordered into rows or matrices or be randomly distributed, or be grown in any other suitable configuration. The crop rows are generally spaced between 2 inches and 45 inches apart (e.g. as determined from the longitudinal row axis), but can alternatively be spaced any suitable distance apart, or have variable spacing between multiple rows.

The plants 102 within each plant field, plant row, or plant field subdivision generally includes the same type of crop (e.g., same genus, same species, etc.), but can alternatively include multiple crops (e.g., a first and a second crop), both of which are to be treated. Each plant 102 can include a stem, arranged superior (e.g., above) the substrate 106, which supports the branches, leaves, and fruits of the plant. Each plant can additionally include a root system joined to the stem, located inferior to the substrate plane (e.g., below ground), that supports the plant position and absorbs nutrients and water from the substrate 106. The plant can be a vascular plant, non-vascular plant, ligneous plant, herbaceous plant, or be any suitable type of plant. The plant can have a single stem, multiple stems, or any number of stems. The plant can have a tap root system or a fibrous root system. The substrate 106 is soil but can alternatively be a sponge or any other suitable substrate.

The detection mechanism 110 is configured to identify a plant for treatment. As such, the detection mechanism 110 can include one or more sensors for identifying a plant. For example, the detection mechanism 110 can include a multispectral camera, a stereo camera, a CCD camera, a single lens camera, a CMOS camera, hyperspectral imaging system, LIDAR system (light detection and ranging system), a depth sensing system, dynamometer, IR camera, thermal camera, humidity sensor, light sensor, temperature sensor, or any other suitable sensor. In one embodiment, and described in greater detail below, the detection mechanism 110 includes an array of image sensors configured to capture an image of a plant. In some example systems, the detection mechanism 110 is mounted to the mounting mechanism 140, such that the detection mechanism 110 traverses over a geographic location before the treatment mechanism 120 as the farming machine 100 moves through the geographic location. However, in some embodiments, the detection mechanism 110 traverses over a geographic location at substantially the same time as the treatment mechanism 120. In an embodiment of the farming machine 100, the detection mechanism 110 is statically mounted to the mounting mechanism 140 proximal the treatment mechanism 120 relative to the direction of travel 115. In other systems, the detection mechanism 110 can be incorporated into any other component of the farming machine 100.

The treatment mechanism 120 functions to perform treatment actions. For example, the treatment mechanism 120 functions to apply a treatment action to an identified plant 102. In the example of FIGS. 1A-1C, the treatment mechanism 120 applies the treatment to the treatment area 122 as the farming machine 100 moves in a direction of travel 115. The effect of the treatment can include plant necrosis, plant growth stimulation, plant portion necrosis or removal, plant portion growth stimulation, or any other suitable treatment effect as described above. The treatment can include plant 102 dislodgement from the substrate 106, severing the plant (e.g., cutting), plant incineration, electrical stimulation of the plant, fertilizer or growth hormone application to the plant, watering the plant, light or other radiation application to the plant, injecting one or more working fluids into the substrate 106 adjacent the plant (e.g., within a threshold distance from the plant), or otherwise treating the plant. In one embodiment, the treatment mechanisms 120 are an array of spray treatment mechanisms. The treatment mechanisms 120 may be configured to spray one or more of: an herbicide, a fungicide, water, or a pesticide. The treatment mechanism 120 is operable between a standby mode, wherein the treatment mechanism 120 does not apply a treatment, and a treatment mode, wherein the treatment mechanism 120 is controlled by the control system 130 to apply the treatment. However, the treatment mechanism 120 can be operable in any other suitable number of operation modes.

The farming machine 100 may include one or more treatment mechanisms 120. A treatment mechanism 120 may be fixed (e.g., statically coupled) to the mounting mechanism 140 or attached to the farming machine 100 relative to the detection mechanism 110. Alternatively, the treatment mechanism 120 can rotate or translate relative to the detection mechanism 110 and/or mounting mechanism 140. In one variation, the farming machine 100 includes a single treatment mechanism, wherein the treatment mechanism 120 is actuated or the farming machine 100 moved to align the treatment mechanism 120 active area 122 with the targeted plant 102. In a second variation, the farming machine 100 includes an assembly of treatment mechanisms, wherein a treatment mechanism 120 (or subcomponent of the treatment mechanism 120) of the assembly is selected to apply the treatment to the identified plant 102 or portion of a plant in response to identification of the plant and the plant position relative to the assembly. In a third variation, such as shown in FIGS. 1A-1C, the farming machine 100 includes an array of treatment mechanisms 120, wherein the treatment mechanisms 120 are actuated or the farming machine 100 is moved to align the treatment mechanism 120 active areas 122 with the targeted plant 102 or plant segment.

The farming machine 100 includes a control system 130 for controlling operations of system components. The control system 130 can receive information from and/or provide input to the detection mechanism 110, the verification mechanism 150, and the treatment mechanism 120. The control system 130 can be automated or can be operated by an operator. In some embodiments, the control system 130 may be configured to control operating parameters of the farming machine 100 (e.g., speed, direction). The control system 130 also controls operating parameters of the detection mechanism 110. Operating parameters of the detection mechanism 110 may include processing time, location and/ or angle of the detection mechanism 110, image capture intervals, image capture settings, etc. The control system 130 may be a computer, as described in greater detail below in relation to FIG. 11. The control system 130 can apply one or more models to identify one or more plants in the field. The control system 130 may be coupled to the farming machine 100 such that an operator (e.g., a driver) can interact with the control system 130. In other embodiments, the control system 130 is physically removed from the farming machine 100 and communicates with system components (e.g., detection mechanism 110, treatment mechanism 120, etc.) wirelessly. In some embodiments, the control system 130 is an umbrella term that includes multiple networked systems distributed across different locations (e.g., a system on the farming machine 100 and a system at a remote location). In some embodiments, one or more processes are performed by another control system. For example, the control system 130 receives farming action instructions from another control system.

In some configurations, the farming machine 100 includes a mounting mechanism 140 that functions to provide a mounting point for the system components. In one example, the mounting mechanism 140 statically retains and mechanically supports the positions of the detection mechanism 110, the treatment mechanism 120, and the verification mechanism 150 relative to a longitudinal axis of the mounting mechanism 140. The mounting mechanism 140 is a chassis or frame but can alternatively be any other suitable mounting mechanism. In the embodiment of FIGS. 1A-1C, the mounting mechanism 140 extends outward from a body of the farming machine 100 in the positive and negative x-direction (in the illustrated orientation of FIGS. 1A-1C) such that the mounting mechanism 140 is approximately perpendicular to the direction of travel 115. The mounting mechanism 140 in FIGS. 1A-1C includes an array of treatment mechanisms 120 positioned laterally along the mounting mechanism 140. In alternate configurations, there may be no mounting mechanism 140, the mounting mechanism 140 may be alternatively positioned, or the mounting mechanism 140 may be incorporated into any other component of the farming machine 100.

The farming machine 100 includes a first set of coaxial wheels and a second set of coaxial wheels, wherein the rotational axis of the second set of wheels is parallel with the rotational axis of the first set of wheels. In some embodiments, each wheel in each set is arranged along an opposing side of the mounting mechanism 140 such that the rotational axes of the wheels are approximately perpendicular to the mounting mechanism 140. In FIGS. 1A-1C, the rotational axes of the wheels are approximately parallel to the mounting mechanism 140. In alternative embodiments, the system can include any suitable number of wheels in any suitable configuration. The farming machine 100 may also include a coupling mechanism 142, such as a hitch, that functions to removably or statically couple to a drive mechanism, such as a tractor, more to the rear of the drive mechanism (such that the farming machine 100 is dragged behind the drive mechanism), but can alternatively be attached to the front of the drive mechanism or to the side of the drive mechanism. Alternatively, the farming machine 100 can include the drive mechanism (e.g., a motor and drive train coupled to the first and/or second set of wheels). In other example systems, the system may have any other means of traversing through the field.

In some configurations, the farming machine 100 additionally includes a verification mechanism 150 that functions to record a measurement of the ambient environment of the farming machine 100. The farming machine may use the measurement to verify or determine the extent of plant treatment. The verification mechanism 150 records a measurement of the geographic area previously measured by the detection mechanism 110. The verification mechanism 150 records a measurement of the geographic region encompassing the plant treated by the treatment mechanism 120. The verification mechanism 150 measurement can additionally be used to empirically determine (e.g., calibrate) treatment mechanism operation parameters to obtain the desired treatment effect. The verification mechanism 150 can be substantially similar (e.g., be the same type of mechanism as) to the detection mechanism 110 or can be different from the detection mechanism 110. In some embodiments, the verification mechanism 150 is arranged distal the detection mechanism 110 relative the direction of travel, with the treatment mechanism 120 arranged there between, such that the verification mechanism 150 traverses over the geographic location after treatment mechanism 120 traversal. However, the mounting mechanism 140 can retain the relative positions of the system components in any other suitable configuration. In other configurations of the farming machine 100, the verification mechanism 150 can be included in other components of the system.

In some configurations, the farming machine 100 may additionally include a power source, which functions to power the system components, including the detection mechanism 110, control system 130, and treatment mechanism 120. The power source can be mounted to the mounting mechanism 140, can be removably coupled to the mounting mechanism 140, or can be separate from the system (e.g., located on the drive mechanism). The power source can be a rechargeable power source (e.g., a set of rechargeable batteries), an energy harvesting power source (e.g., a solar system), a fuel consuming power source (e.g., a set of fuel cells or an internal combustion system), or any other suitable power source. In other configurations, the power source can be incorporated into any other component of the farming machine 100.

In some configurations, the farming machine 100 may additionally include a communication apparatus, which functions to communicate (e.g., send and/or receive) data between the control system 130 and a set of remote devices. The communication apparatus can be a Wi-Fi communication system, a cellular communication system, a short-range communication system (e.g., Bluetooth, NFC, etc.), or any other suitable communication system.

Figure 2:
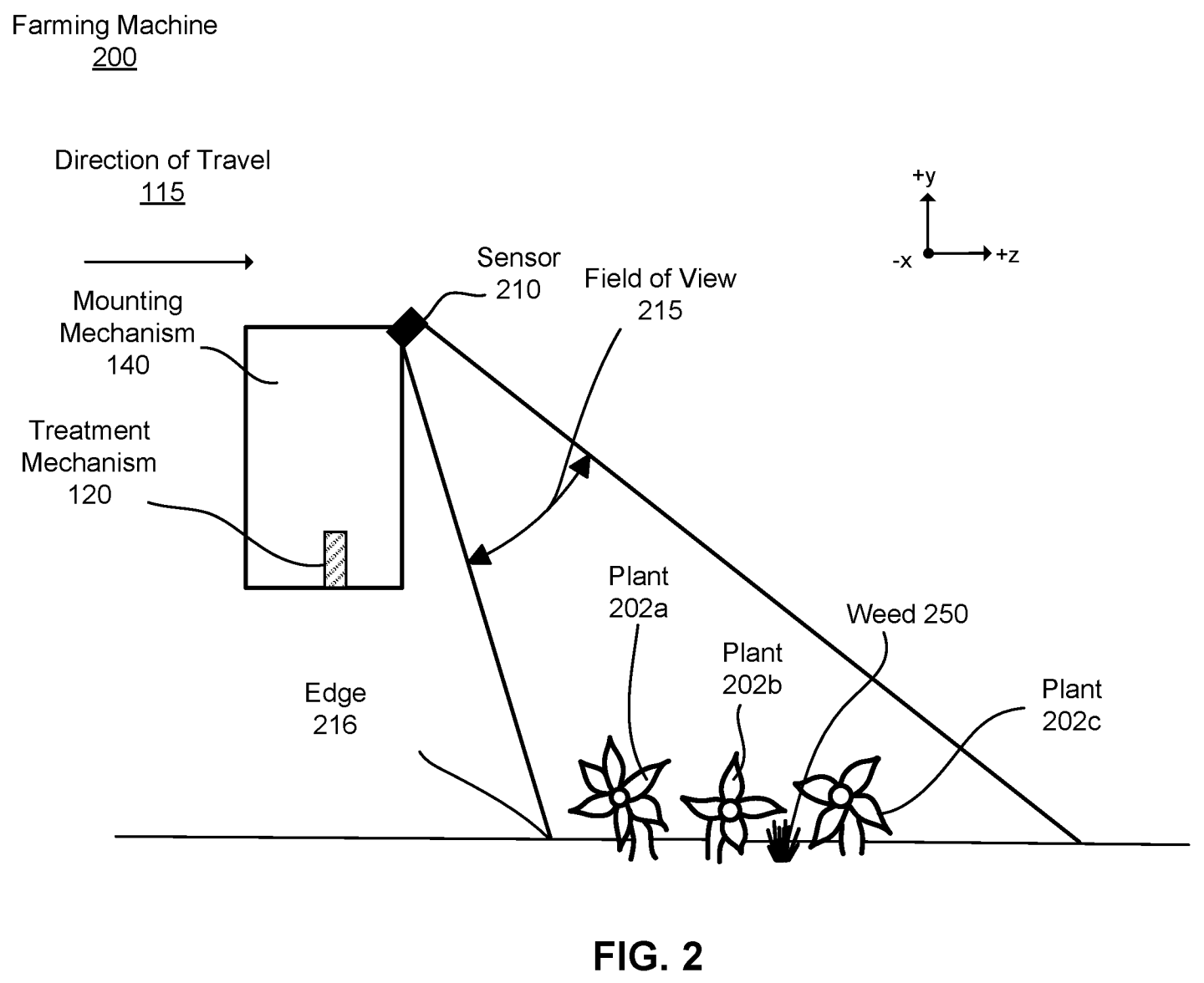

FIG. 2 illustrates a cross-sectional view of a farming machine including a sensor configured to capture an image of one or more plants, in accordance with some example embodiments. The farming machine 200 may be similar to any of the farming machines described in regard to FIG. 1A-1C. In the embodiment of FIG. 2, the farming machine includes a sensor 210. Here, the sensor 210 is a camera (e.g., RGB camera, near infrared camera, ultraviolet camera, or multi-spectral camera), but could be another type of image sensor suitable for capturing an image of plants in a field. The farming machine 200 can include additional sensors mounted along the mounting mechanism 140. The additional sensors may be the same type of sensor as sensor 210 or different types of sensors.

In FIG. 2, sensor 210 has a field of view 215. The field of view 215, herein, is the angular extent of an area captured by a sensor 210. Thus, the area captured by the sensor 210 (e.g., the field of view 215) may be affected by properties (i.e., parameters) of the sensor 210. For example, the field of view 215 may be based on, for example, the size of the lens and the focal length of the lens. Additionally, the field of view 215 may depend on an orientation of the sensor. For example, an image sensor with a tilted orientation may generate an image representing a trapezoidal area of the field, while an image sensor with a downwards orientation may generate an image representing a rectangular area of the field. Other orientations are also possible.

In FIG. 2, the sensor 210 is tilted. More specifically, the sensor 210 is mounted to a forward region of the mounting mechanism 140, and the sensor 210 is tilted downwards towards the plants. Described herein, a downwards tilt angle is defined as an angle between the z-axis and the negative y-axis. The field of view 215 includes plants 202*a*, 202*b*, 202*c* and weed 250. The distance between the sensor 210 and each plant varies based on the location of the plant and the height of the plant. For example, plant 202*c* is farther than plant 202*a* from the sensor 210. The sensor 210 can be tilted in other directions.

FIG. 2 also illustrates a treatment mechanism 120 of the farming machine. Here, the treatment mechanism 120 is located behind the sensor 210 along the z-axis, but it could be in other locations. Whatever the orientation, the sensor

210 is positioned such that the treatment mechanism 120 traverses over a plant after the plant passes through the field of view 215. More specifically, as the farming machine 100 travels towards the plant 202, the plant 202 will exit the field of view 205 at an edge 216 of the field of view nearest the treatment mechanism 120. The distance between the edge 216 and the treatment mechanism 120 is the lag distance. The lag distance allows the control system 130 to capture and process an image of a plant before the treatment mechanism 120 passes over the plant. The lag distance also corresponds to a lag time. The lag time is an amount of time the farming machine has before the treatment mechanism 120 passes over the plant 202. The lag time is an amount of time calculated from farming machine operating conditions (e.g., speed) and the lag distance.

In some configurations, the treatment mechanism 120 is located approximately in line with the image sensor 210 along an axis parallel to the y-axis but may be offset from that axis. In some configurations, the treatment mechanism 120 is configured to move along the mounting mechanism 140 in order to treat an identified plant. For example, the treatment mechanism may move up and down along a y-axis to treat a plant. Other similar examples are possible. Additionally, the treatment mechanism 120 can be angled towards or away from the plants.

In various configurations, a sensor 210 may have any suitable orientation for capturing an image of a plant. Further, a sensor 210 may be positioned at any suitable location along the mounting mechanism 140 such that it can capture images of a plant as a farming machine travels through the field.

III. System Environment

Figure 3:
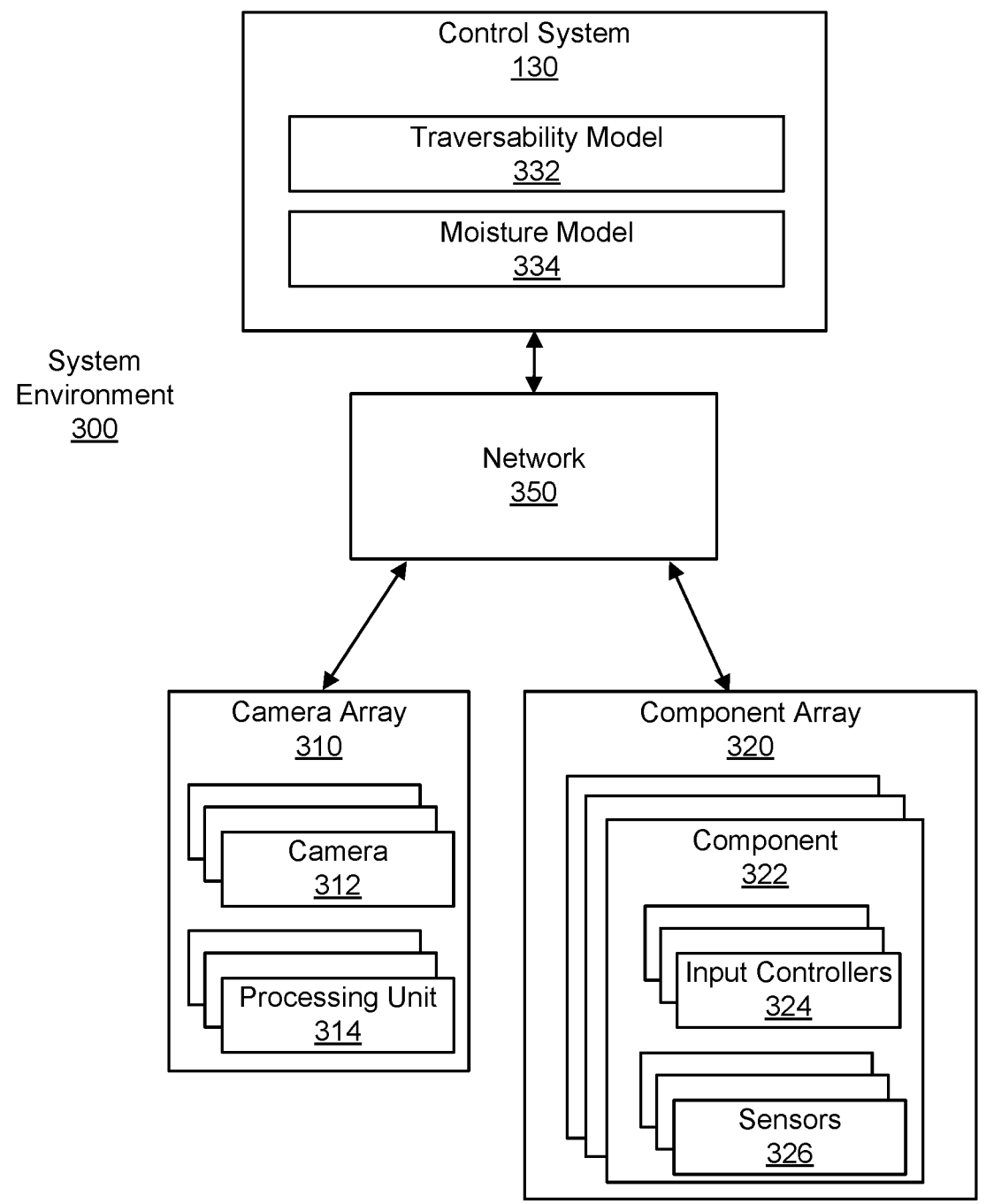
FIG. 3 illustrates a block diagram of the system environment for the farming machine, in accordance with an example embodiment.

FIG. 3 illustrates a block diagram of the system environment for the farming machine, in accordance with an example embodiment. In this example, the control system 310 is connected to a camera array 320 and component array 320 via a network 350 within the system environment 300.

The camera array 310 includes one or more cameras 312 (also referred to as image sensors). The cameras 312 may be a detection mechanism 110 as described with reference to FIGS. 1A-1C. Each camera 312 in the camera array 310 may be controlled by a processing unit 314 (e.g., a graphics processing unit). In some examples, more than one camera 312 may be controlled by a single processing unit 314. The array 310 captures image data of the scene around the farming machine 100 (and possibly the farming machine itself). The captured image data may be sent to the control system 130 via the network 350 or may be stored or processed by other components of the farming machine 100.

The component array 320 includes one or more components 322. Components 322 are elements of the farming machine that can take farming actions (e.g., a treatment mechanism 120). As illustrated, each component has one or more input controllers 324 and one or more sensors, but a component may include only sensors or only input controllers. An input controller controls the function of the component. For example, an input controller may receive machine commands via the network and actuate the component in response. A sensor 326 generates measurements within the system environment. The measurements may be of the component, the farming machine, or the environment surrounding the farming machine. For example, a sensor 326 may measure a configuration or state of the component 322

(e.g., a setting, parameter, power load, etc.), or measure an area surrounding a farming machine (e.g., moisture, temperature, etc.).

The control system 130 receives information from the camera array 310 and component array 320 and generates instructions for farming actions. The control system 130 may include one or more models and instructions to operate the farming machine in a field with moisture. For example, the control system 130 includes instructions for implementing one or more steps described with reference to FIGS. 5 and 7. In the example of FIG. 3, the control system 130 includes a traversability model 332 and a moisture model 334. These models are further described with reference to FIGS. 5 and 7.

The network 350 connects nodes of the system environment 300 to allow microcontrollers and devices to communicate with each other. In some embodiments, the components are connected within the network as a Controller Area Network (CAN). In this case, within the network each element has an input and output connection, and the network 350 can translate information between the various elements. For example, the network 350 receives input information from the camera array 310 and component array 320, processes the information, and transmits the information to the control system 130. The control system 130 generates a farming action based on the information and transmits instructions to implement the farming action to the appropriate component(s) 322 of the component array 320.

Additionally, the system environment 300 may be other types of network environments and include other networks, or a combination of network environments with several networks. For example, the system environment 300, can be a network such as the Internet, a LAN, a MAN, a WAN, a mobile wired or wireless network, a private network, a virtual private network, a direct communication line, and the like.

IV. Operating a Farming Machine in Field with Moisture

As described above, a farming machine (e.g., farming machine 100) is configured to move through a field and perform one or more farming actions (e.g., treating one or more plants) in the field. Portions of the field may include moisture, such as puddles or mud patches. A control system (e.g., control system 130) associated with the farming machine may include one or more models to help the farming machine operate (e.g., perform one or more actions) in the field with moisture. In particular, the control system may employ a traversability model to reduce the likelihood of the farming machine becoming immobilized (e.g., getting stuck) in a portion of the field, and may employ a moisture model to reduce the likelihood of the farming machine performing an action that will damage a portion of the field.

Figure 4:
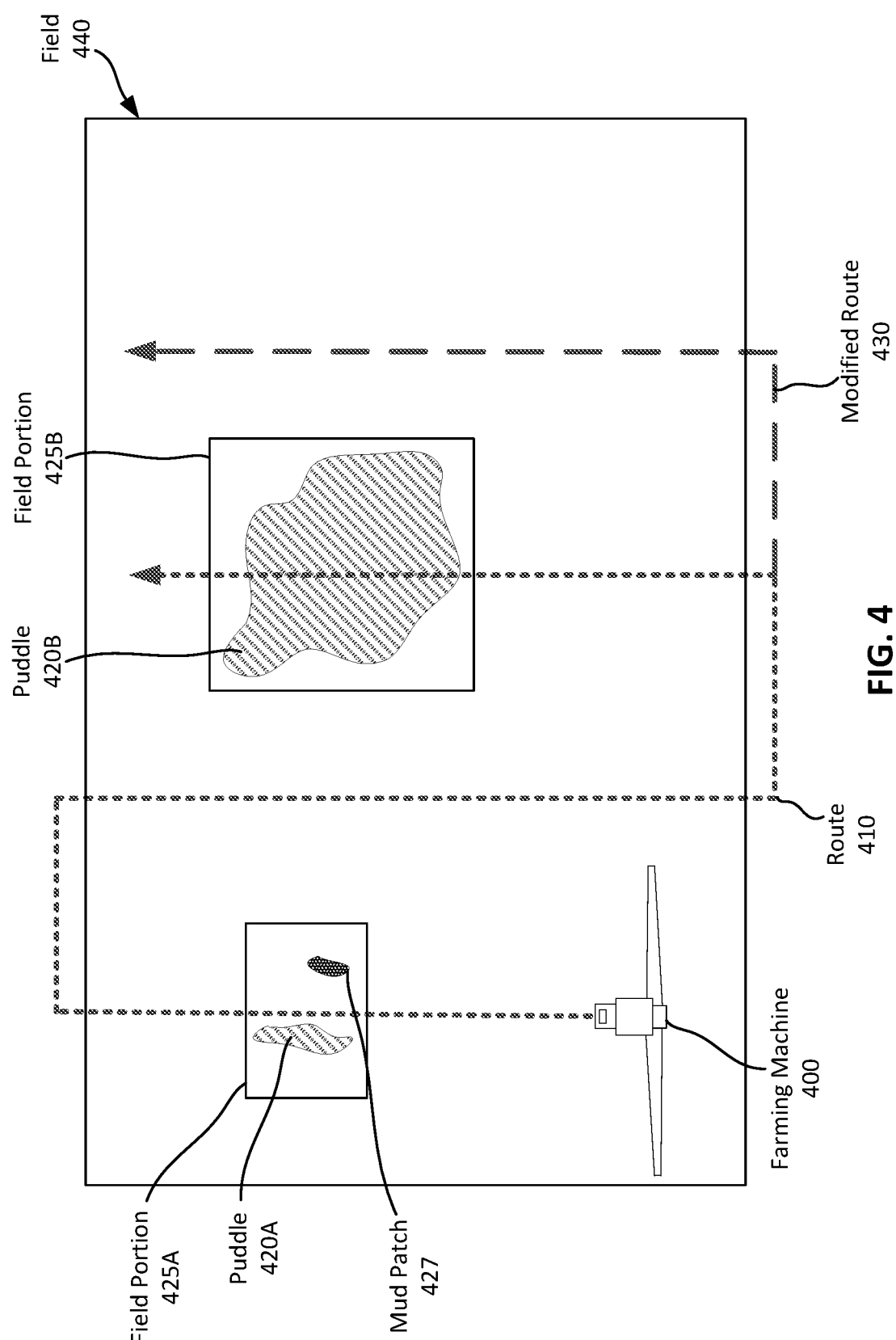
FIG. 4 is an overhead view of a farming machine moving along a route through a field with moisture, in accordance with an example embodiment.

FIG. 4 is an overhead view of a farming machine 400 moving along a route 410 through a field 440 with moisture, according to an embodiment. Portions of the field (e.g., portions 425A and 425B) include moisture in the form of puddles of liquid 420 and a mud patch 427. In the example of FIG. 4, puddle 420B is significantly larger than puddle 420A. The farming machine 400 (e.g., via the control system 130) can analyze the moisture in the field and determine whether the farming machine 400 will get stuck or damage the field as it moves through portions 425 of the field that include the puddles 420 and mud patch 427. In the example of FIG. 4, the control system determines that the farming machine can move through the field portion 425A (including puddle 420A and mud patch 427). However, the farming machine 400 determines that it cannot or should not move through the field portion 425B (including puddle 420B). For example, the farming machine 400 determines that the portion 425B has a traversability difficulty above the traversability capability of the farming machine 400. In another example, the farming machine 400 determines that the likelihood of the farming machine 400 damaging the field portion 425B is above a likelihood threshold.

In response to the farming machine 400 determining that it cannot or should not move through the field portion 425B (e.g., the farming machine determines the field portion 425B is untraversable or there is a high likelihood that the farming machine will damage the field portion 425B), the farming machine generates a modified route 430 for the farming machine 400. By traveling along the modified route 430, the farming machine 400 will avoid the portion of the field that includes puddle 420B. If the farming machine 400 is performing treatment actions in the field, the route may be modified so that portions of the field around puddle 420B are still treated by the farming machine. For example, the farming machine 400 may drive around the puddle and back up to the puddle 420B to reduce the amount of unworked ground around the puddle 420B.

IV.A Applying the Traversability Model

FIG. 5 illustrates a method for operating in a field with moisture by a farming machine (e.g., farming machine 100), in accordance with an example embodiment. The method 500 may be performed from the perspective of the control system 130. The method 500 can include greater or fewer steps than described herein. Additionally, the steps can be performed in different order, or by different components than described herein.

A farming machine (e.g., farming machine 100) moves 510 along a route in a field towards a portion of the field including moisture. An example of this is illustrated in FIG. 4. While this disclosure is described in the context of a farming machine moving through a field, the farming machine may move through other types of terrain such as roads, streets, etc. As described herein, a portion of the field (also referred to as a field portion) is a subsection of the field that is smaller than the entire field. A field portion is large enough to include one or more bodies of moisture, which are large enough for the farming machine to potentially get stuck or large enough that the farming machine can potentially damage the field if it moves through the field portion. The farming machine may be actively controlled by an operator in the farming machine, remotely controlled by an operator, or autonomous. If the farming machine is autonomous, it may still receive instructions from an operator.

The control system accesses 520 an image of the portion of the field. The image includes a group of pixels that indicate a moisture level of the portion of the field. One or more image sensors capture the image. Example image sensors that can capture the image are described with reference to the detection mechanism 110. The image sensors may be coupled to the farming machine and oriented to capture the portion of the field (e.g., a portion of the field in front of the farming machine). The image sensors may capture images as the farming machine moves along the route. FIGS. 6A-6E are example images of fields and roads with moisture that may be accessed by the control system. FIGS. 6A-6E are further described with reference to step 530.

Returning to FIG. 5, the control system applies 530 a traversability model to the image of the portion of the field. The traversability model determines a moisture level of the portion of the field and determines a traversability difficulty for the portion of the field using the moisture level. Additionally or alternatively, in some embodiments, the traversability model determines whether a field portion is traversable or untraversable. Determining whether a field portion is traversable or untraversable may be based on the moisture level. If a traversable field portion is detected, the farming machine may move through the field portion. If an untraversable field portion is detected, an obstacle event may be triggered so that the farming machine performs a farming action, such as modifying the farming machine's route so that it does not move through the field portion.

Moisture as described herein can include liquid (e.g., water) on the surface of the ground (e.g., a puddle, body, or pool of water), liquid in the soil (e.g., mud), and liquid in the air (e.g., rain or fog). The moisture level (also referred to as a measure of moisture) describes an amount of moisture in, on, or above the soil in the field portion. The level may be an objective measure, such as an estimate in gallons of the amount of moisture or the shape and size of a body of moisture (e.g., the depth, width, and length a body of liquid). The level can alternatively be on a scale, such as one to ten, where one indicates no moisture and ten indicates the presence of a large amount of moisture. If the portion of the field includes multiple bodies of moisture, the traversability model may determine multiple moisture levels e.g., a moisture level for each body of moisture. In some embodiments, the traversability model distinguishes between liquid on the surface, liquid in the soil, and liquid in the air and determines a moisture level for each. For example, the control system determines a moisture level for a pool of liquid on the surface and determines another level for mud around the pool of liquid. In some embodiments, the traversability model detects any possible obstructions due to moisture and quantifies how much of it is on a path of the farming machine 400 or the percentage of the obstacle in the FOV (field of view) of the image sensor.

The control system determines the moisture level for a field portion, for example, by applying a moisture model. The control system determines the moisture level by analyzing one or more groups of pixels in the image to identify moisture and determine an amount of moisture in the image. For example, visual properties such as texture, reflection, and saturation indicate the presence, location, and amount of moisture. In some embodiments, the detection of polarized light may be used to detect the presence of liquid. In another example, pixel values from a thermal sensor are analyzed (e.g., since moisture can be identified by comparing local temperature values). In some embodiments, multiple images are used by the traversability model. For example, images captured by different types of image sensors or images captured at different views are analyzed together to determine the moisture level.

In addition to analyzing pixels of the image, the traversability model may receive non-visual information to determine the moisture level of the portion of the field, such as temperature, humidity, wind, weather data, topography, and soil maps. For example, the control system accesses current or historical weather data for the portion of the field to determine the moisture level.

As stated earlier, the traversability model uses the moisture level to determine a traversability difficulty for the portion of the field. The traversability difficulty quantifies a level of difficulty for a vehicle to move through the portion of the field having the moisture level. As described herein, a higher traversability difficulty indicates a field portion is less traversable and a lower traversability difficulty indicates a field portion is more traversable. Generally, a high moisture level results in a high traversability difficulty and vice versa, however the relationship may not be linear, and the traversability difficulty may depend on other factors, some of which are further described below. The relationship between moisture level and traversability difficulty may be machine learned, for example, by training the traversability model with historical traversability data. Historical traversability data may include images of field portions, moisture levels of moisture in the images, and traversability difficulty scores associated with the field portions. The traversability difficulty is generally determined prior to the farming machine moving through the field portion. However, a traversability difficulty may be determined or updated if/when the farming machine moves through the field portion.

In some embodiments, the traversability difficulty indicates a likelihood of a vehicle losing traction or getting stuck. In another example, the traversability difficulty is on a scale, such as one to ten, where one indicates almost any vehicle can move through the field portion and ten indicates only highly specialized vehicles can move through the field portion. In other embodiments, the traversability difficulty specifies characteristics of vehicles that can move through the portion of the field. For example, the traversability difficulty specifies a wheel type (e.g., wheel or track), a wheel size, a tread type, an engine/motor type, a drive type (e.g., front, rear, or all-while drive), a make, a model, a weight, a treatment mechanism, and/or coupling mechanism of a vehicle that can move through the portion of the field.

While the traversability difficulty is based on the moisture level of the field portion, the traversability difficulty may also be based on additional factors, such as soil type or gradient. For example, the traversability model includes a weighted model with a weight for each factor, where each weight indicates how strongly its corresponding factor affects the traversability difficulty. The additional factors may be determined by the traversability model. Example additional factors are described below.

An example additional factor is the one or more soil types in the portion of the field. One or more soil types may be determined by analyzing pixels of an image of the field portion (soil types may have identifiable colors and textures), accessing a soil map, and/or receiving input from an operator of the farming machine. Example soil types include clay, loam, sand, silt, gravel, asphalt, and concrete. Since moisture (and the amount of moisture) may affect the traversability of soil types differently, determining a soil type of a field portion can assist in determining the traversability difficulty. For example, moisture in sand generally has no effect on traversability, but moisture in clay or loam generally decreases traversability (i.e., increases the traversability difficulty). If multiple soil types are identified, the traversability of the combination of the soil types may be considered (e.g., the presence of gravel in clay may make it more traversable).

Another example factor is the gradient of the field portion of the field (also referred to as the grade or slope). Generally, higher a gradient decreases the traversability for a field portion. In some embodiments, a slope larger than 9 degrees renders the field portion untraversable. The gradient may be determined by analyzing pixels of the image, accessing a topography map, and/or receiving input from an operator of the farming machine.

Other indicators of the traversability difficulty include:

(1) The visibility of an edge of a body of moisture (also referred to as the boundary or outline). If an edge of a body of moisture is visible and distinct, it may indicate that the soil around the body is firm and dry. Thus, an identifiable edge of a body may decrease the traversability difficulty.

(2) An amount of plant matter or debris in a body of moisture. The presence of plant matter or debris may decrease the traversability difficulty because plant matter and debris may reduce the likelihood of loss of traction. Additionally, the presence of plant matter and debris sticking up through a body of liquid may indicate that the body is not deep.

(3) A depth of track marks. The depth of track marks may indicate how firm the soil is. Deep track marks may indicate a field portion is less traversable, and shallow track marks may indicate a field portion is more traversable. The size of dirt clods (e.g., made by the farming machine as it moves through the field) may also indicate how firm the soil is. For example, larger dirt clods may indicate a field portion includes more moisture and is less traversable and smaller dirt clods my indicate a field portion includes less moisture and is more traversable.

(4) Movement of a body of liquid. Movement of liquid can make a field portion more difficult to traverse. Thus, a stagnant or slow-moving body may have a lower traversability difficulty than a body with a current (e.g., a river or stream).

These factors may be determined by analyzing pixels in an image of the field portion. In some embodiments, one or more of these factors are part of or contribute to the moisture level. In some embodiments, the traversability difficulty is also based on factors that are not related to moisture, such as the presence of obstacles in the field portion (e.g., a boulder or trench). Descriptions of the moisture level, additional factors, and the traversability difficulty are further described below with reference to FIGS. 6A-6E.

Figure 6A:
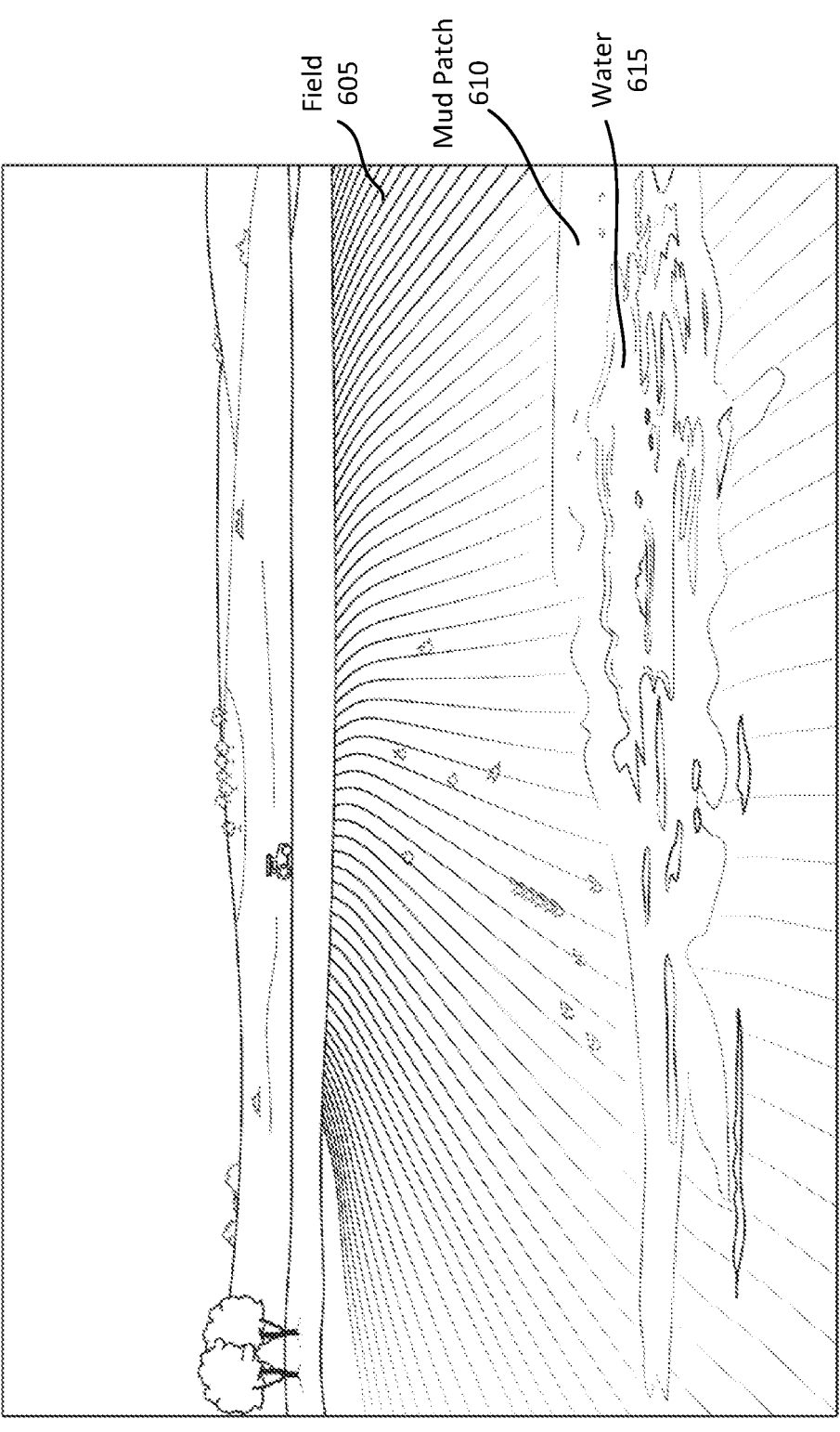
FIGS. 6A-6E are example images of fields and roads with moisture that may be accessed by a control system of the farming machine.

FIG. 6A is an image of a field 605 that includes a mud patch 610 with water 615 in the lower right corner. The amount of moisture may be determined based on the area and depth of the mud patch 610. The area may be determined by comparing the size of the patch 610 to the size of the rows in the field. Similarly, the depth of the mud patch may be determined by comparing the height of the rows relative to the surface of the water 615 and mud in the patch 610. The depth of the water 615 does not seem deep since water in the mud is generally below the tops of the rows. Since the edges of the mud patch 610 are not clearly identifiable, this may increase the traversability difficulty of the mud patch.

Figure 6B:
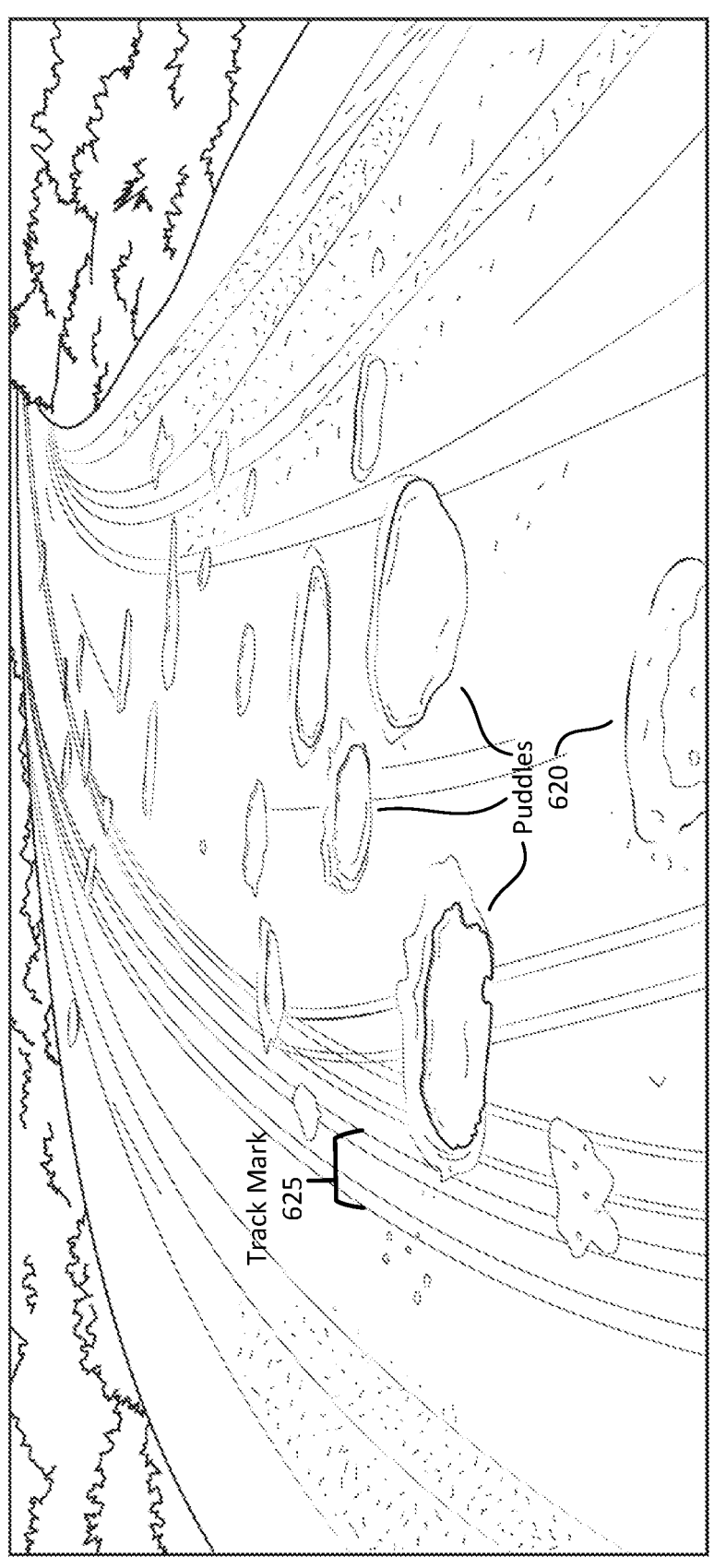

FIG. 6B is an image of a road that includes circular puddles 620. The edges of the puddles 620 are distinct, which may indicate that the ground around the puddles 620 is firm and dry. This is supported by the presence of faint track marks 625 in the soil around the puddles 620. Additionally, the size of the puddles 620 is small (e.g., determined by comparing the puddles 620 to the width of the road). All of these features indicate that the moisture level and traversability difficulty are low for the road in FIG. 6B.

Figure 6C:
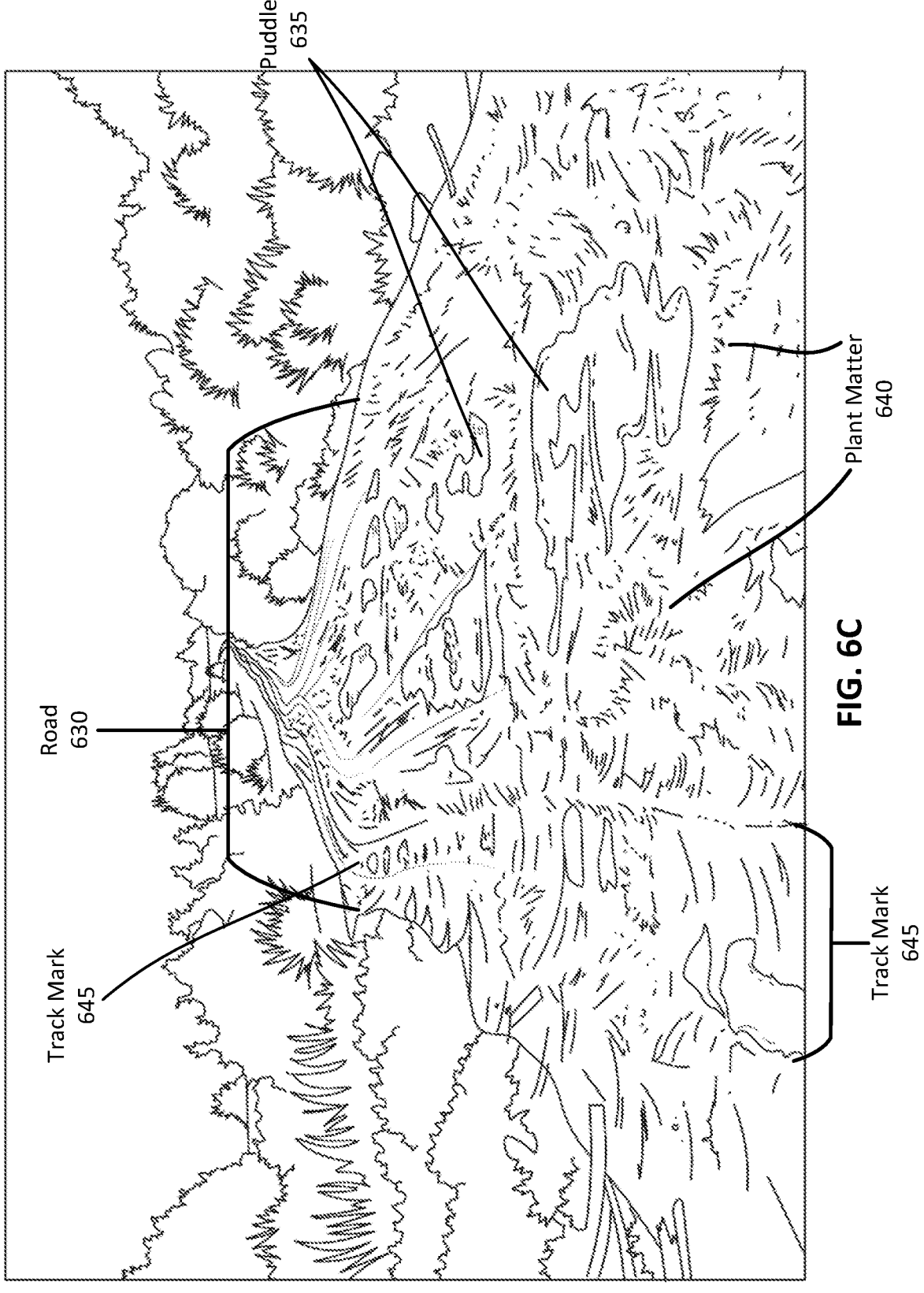

FIG. 6C is another image of a road 630. The road 630 is muddy and includes puddles 635 with edges that are less defined than in FIG. 6B. This indicates that the road 630 is less traversable than the road in FIG. 6B. However, the mud and puddles include plant matter 640, which increases the traversability. FIG. 6C also includes track marks 645 that are deeper than the track marks 625 in FIG. 6B, which may decrease the traversability.

Figure 6D:
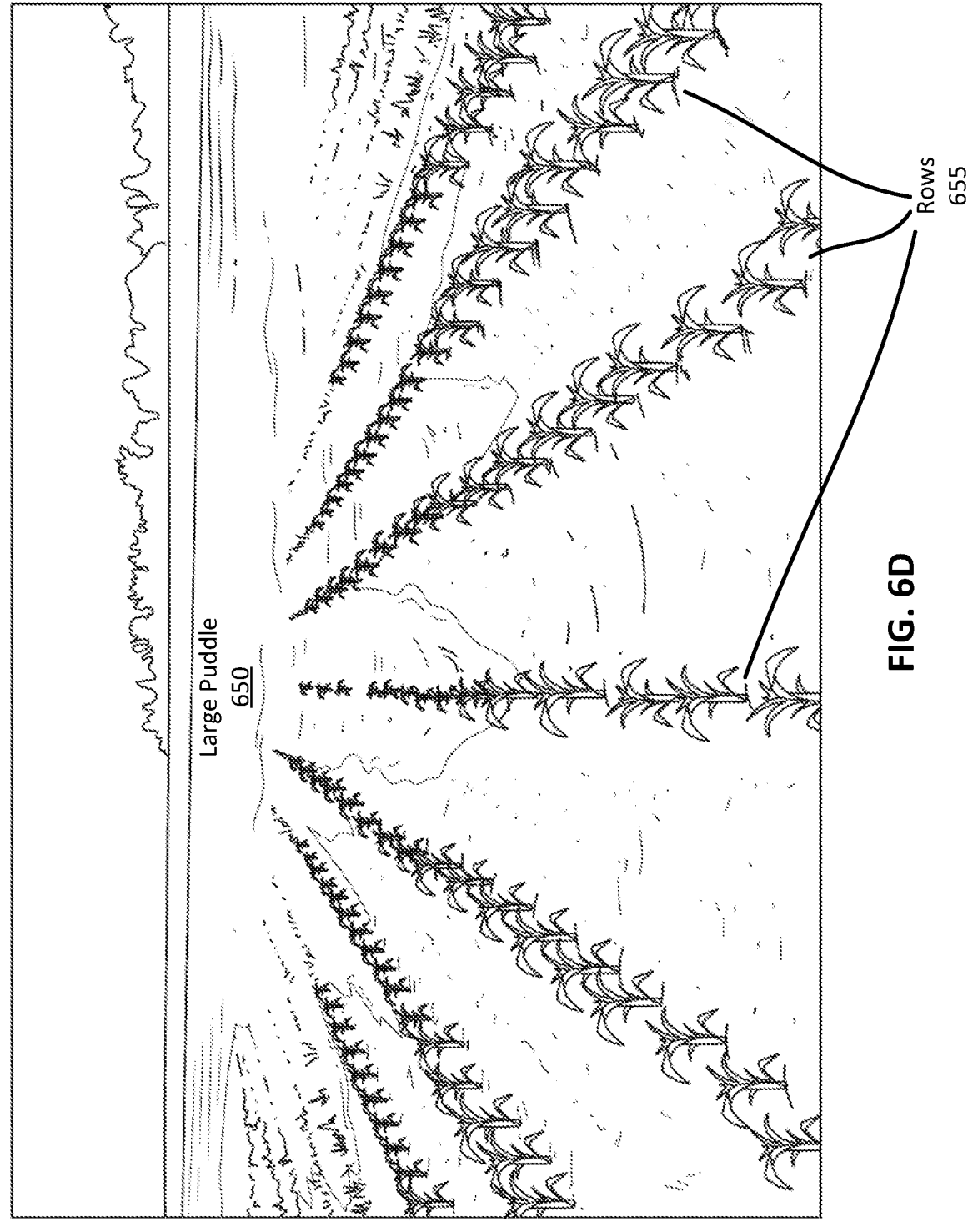
Figure 6E:
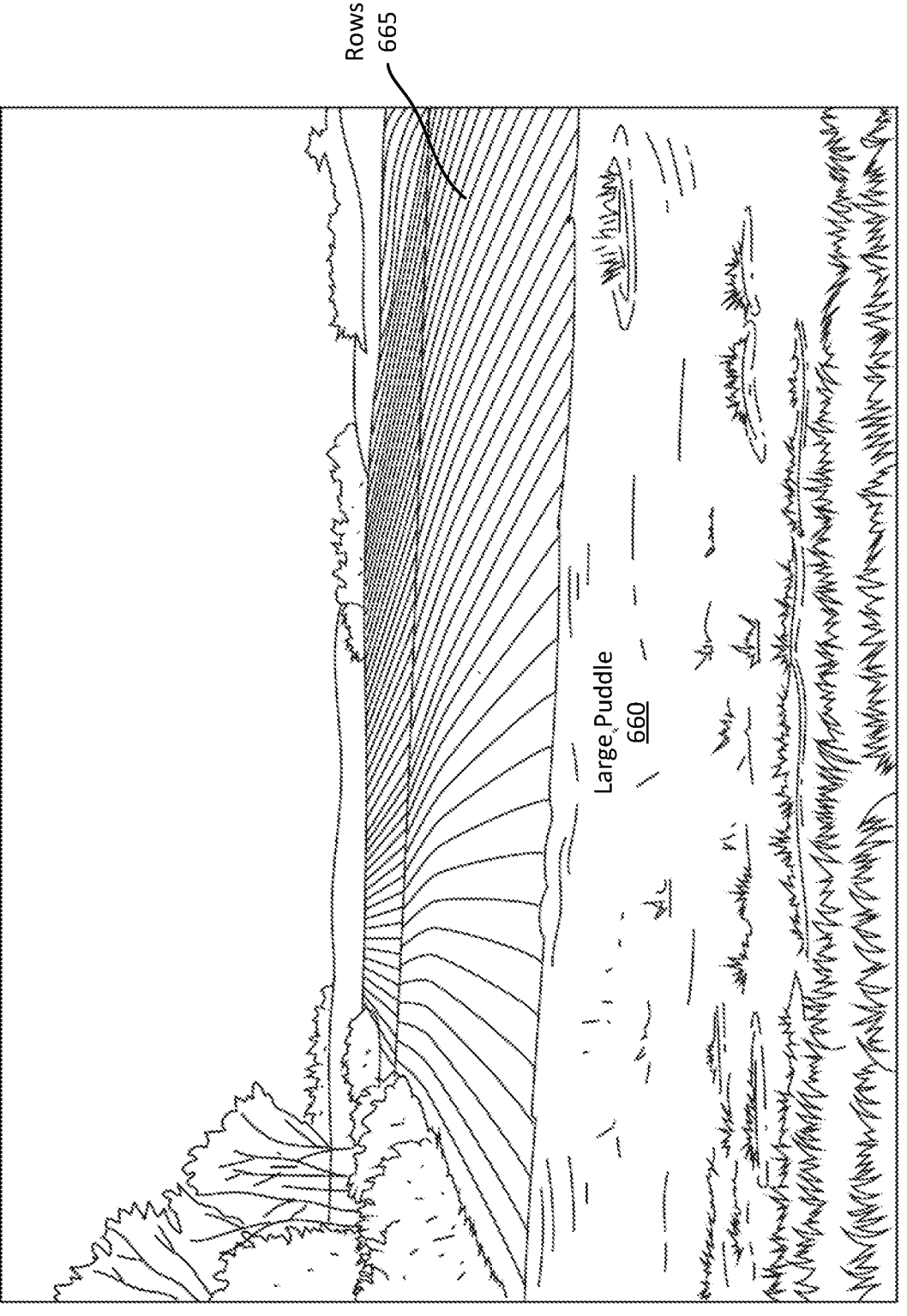

FIGS. 6D and 6E are images of fields with large puddles (650 and 660). Generally, small puddles between rows are traversable. However, if standing water goes above the rows (e.g., rows 655 and 665), the field may become non-traversable.

Referring back to FIG. 5, the farming machine performs 540 a farming action (e.g., after receiving instructions from the control system) in the field responsive to determining the traversability difficulty is above a traversability capability of the farming machine.

The traversability capability quantifies an ability of the farming machine to travel through fields with moisture. As described herein, a higher traversability capability indicates the farming machine can traverse more difficult terrain. The traversability capability may have a same unit of measurement or be on a same scale as the traversability difficulty so that the values can be directly compared. The traversability capability of the farming machine may be based on operational parameters of the farming machine (e.g., speed and torque) and characteristics that may affect the farming machine's ability to traverse terrain. Example farming machine characteristics include a wheel type (e.g., wheel or tracks), a wheel size, a tread type, an engine/motor type, a drive type (e.g., front, rear, or all-while drive), a make, a model, a weight, a fuel level, a tank level for a sprayer, a treatment mechanism, and/or coupling mechanism of the farming machine. Values of these characteristics may be determined from sensors of the farming machine. One or more of the characteristics may be variable. For example, the weight of the farming machine changes over time as the farming machine sprays plants in the field and consumes fuel. Thus, the traversability capability may be a fixed value or, in some embodiments, a variable quantity that changes over time based on the real time operational parameters and characteristics of the farming machine. In some embodiments, the traversability capability is specific to a treatment action performed by the farming machine as it moves through the field. For example, the farming machine may have a first traversability capability if it is applying a first treatment (e.g., tilling the field) and a second traversability capability if it is applying a second treatment (e.g., spraying plants).

A farming action in the context of step 540 is an action performed by the farming machine (e.g., via the control system) and intended to prevent or reduce the likelihood of the farming machine attempting to traverse an untraversable field portion. In some cases, the farming action modifies (e.g., cancels) an action already being performed by the farming machine. An example farming action includes modifying an operational parameter of the farming machine. Modifying an operational parameter may increase the traversability capability of the farming machine, such as increasing the speed, switching to all-wheel drive, switching from speed-control to torque-control on the drive wheel motors, ceasing to apply power to the wheels so that the farming machine 'coasts' through the field portion, or raising a treatment mechanism, so that the traversability capability is no longer below the traversability difficulty. Another example of a farming action includes sending a warning notification to an operator of the farming machine. In another example, the farming action modifies (e.g., cancels) a treatment action being performed by the farming machine. For example, if a treatment action limits the speed of the farming machine such that it will not have enough speed to traverse the field portion, the farming action may cease the treatment action so the farming machine can increase its speed.

In some embodiments, the farming action modifies the farming machine's route such that it does not move through (or ceases to move through) the portion of the field including moisture (e.g., see description with respect to FIG. 4). If the route is modified, it may be modified so that the farming machine will move through the field portion at a later point in time and/or so that the farming machine will move through the field from a different direction (e.g., modifying the route so that the farming machine moves through the portion while traveling downhill instead of uphill). This may allow time for the conditions at the field portion (e.g., the moisture level) to change. This may also provide the farming machine time or the opportunity to adjust one or more characteristics so it can move through the field portion. For example, the route is modified so that the farming machine moves through the portion with a lighter machine load, such as waiting until the volume in a spray tank or fuel tank has decreased. In another example, the farming machine modifies its weight or weight distribution by using counterweight brackets, shedding unused components, dumping material or transferring material to a storage tank, swapping components like wheels or tracks, disengaging a treatment mechanism (e.g., a plow), or by attaching accessories like skids, skis, or additional idler wheels. In another example, the wheel or track width of the farming machine is modified. In some embodiments, the farming machine, another farming machine (e.g., a helper machine), or an operator may modify the field portion (e.g., by applying sand, laying skids or boards onto the path, or blasting the area with air.)

The traversability difficulty may be determined while the farming machine is moving towards the portion of the field. However, the traversability difficulty may be determined prior to this. For example, an image sensor (e.g., on a scout, drone, aerial imager, or satellite that is physically separate from the farming machine) captures an image of the field portion of the field and the traversability model is applied to the image (e.g., using cloud processing) prior to the farming machine moving through the field. When it is time to move in the field (e.g., later in the day or on another day), farming action instructions may be provided to the farming machine. Said differently, the traversability difficulty may be determined at a first time and the farming machine may perform the farming action based on the traversability difficulty (and the measure of traversability) at a second time, where the second time can occur at any time after the first time. In some embodiments, if the control system determines a traversability difficulty for one or more portions of the field before the farming machine moves in the field, the control system may determine the route based on the determined traversability difficulties (and the traversability capability of the farming machine).

As stated above, a traversability difficulty for a portion of the field may be determined prior to the farming machine moving through the field portion. However, the traversability difficulty may be determined or updated as the farming machine moves through the field portion. Because the farming machine is closer to the portion of the field, the updated traversability difficulty may be more accurate than the previously determined traversability difficulty. For example, a closer view of a body of moisture results in a more accurate determination of the size of the body, and thus, a more accurate traversability difficulty determination. If a traversability difficulty was previously determined for a portion of the field, the farming machine may move through the portion of the field if the traversability difficulty was not above the traversability capability of the farming machine. Below is an example description of updating the traversability difficulty for a farming machine that is traveling through the field portion. The description is in the context of FIG. 5.

Responsive to the farming machine moving through the field portion, the farming machine accesses a second image of the portion of the field from a second image sensor. The image includes a second group of pixels that indicate an updated moisture level of the portion of the field. The control system applies the traversability model to the second image. The traversability model determines the updated moisture level of the portion of the field using the second group of pixels and determines an updated traversability difficulty for the portion of the field using the updated moisture level. In some embodiments, the control system applies a model (e.g., to images captured by side sensors) to examine a previous field portion (that the farming machine moved through) and a future field portion (e.g., along a route) to determine if there is a difference in moisture or traversability difficulty. Responsive to a difference between the traversability difficulty and the updated traversability difficulty being greater than a threshold, the farming machine performs a second farming action.

The second image sensor may be the same image sensor that captured the first image. Alternatively, it may be a different image sensor. For example, the farming machine includes two image sensors. The first image sensor has a field of view that captures a field portion that the farming machine is moving towards, where images from the first image sensor are used to determine a traversability difficulty for the field portion. The second image sensor has a field of view that captures a current field portion that the farming machine is moving through, where images from the second image sensor are used to determine a traversability difficulty for the current field portion. In some embodiments, the second image sensor is positioned to include a view of the farming machine. For example, the second image sensor captures a view of a wheel of the farming machine in contact with the soil (e.g., to detect the presence of mud build up). In this example, an increase in wheel diameter may indicate the presence of mud build up on the tired and a decrease in wheel diameter may indicate the wheel is slipping. In some embodiments, the second image sensor is positioned to view the field behind the farming machine (e.g., to capture the depth of track marks left by the farming machine).

The updated moisture level and updated traversability difficulty may be determined using one or more factors described with reference to step 530. However, now that the farming machine is traveling (or has traveled) through the portion of the field, the farming machine may have access to new data that can additionally or alternatively be used to determine the updated moisture level and updated traversability difficulty. For example, the control system records diagnostic information from one or more diagnostic sensors of the farming machine, where the diagnostic information may indicate an updated moisture level and/or traversability difficulty. For example, a height sensor is mounted to the farming machine at a known height, and information from the height sensor indicates how deep the machine has sunk into the soil. In another example, a hygrometer mounted to the farming machine provides humidity information. In another example, information from a level sensor and/or altimeter may be used to determine the gradient of the field portion. Other example sensors of the farming machine include motion sensors such as inertial measurement units (IMUs) (e.g., to measure cab vibrations of the farming machine), GPS sensors, torque/force sensors, thermal sensors, and draft/load sensors (e.g., on a pin of a chisel plow). Due to the presence of this new data, the traversability model may include a first model to determine the traversability difficulty and a second model to determine the updated traversability difficulty. In some embodiments, if an updated traversability difficulty (or updated moisture level) for a first field portion is significantly different than the traversability difficulty (or moisture level) for the field portion, the updated traversability difficulty may be used to update the traversability difficulty of one or more other field portions. This update may inform route changes for field portions that now exceed a threshold but previously did not.

In addition to the diagnostic information, the control system may use real time operational parameters to determine an updated moisture level and/or traversability difficulty. For example, if the orientation of the farming machine is unresponsive or responds slower than expected to changes in the wheel steering direction, this may indicate an increase in the moisture level and/or traversability difficulty of the field portion. In another example, if the engine/motor power usage is increasing (e.g., due to mud build up), this may indicate an increase in the moisture level and/or traversability difficulty.

Other examples of operational parameters include a gear setting, speed, engine/motor power, engine/motor torque, and engine/motor RPM (revolutions per minute). If the operational parameters are not inherently known, they may be determined using diagnostic information from one or more sensors in the farming machine. For example, the control system determines wheel or track slip of the farming machine. Slip may be determined by comparing diagnostic information from several sensors, such as rotary encoders in the wheels, GPS, and/or ground-facing radar. In another example, the control system monitors control errors. If tracking errors are higher than expected or if the tracking stability is worse than expected (e.g., increased overshoot or settling time), the control system may determine that a field portion includes a higher moisture level and/or traversability difficulty. In some embodiments, the farming machine performs a treatment action, such as spraying something on the soil. Differences in how the spray looks on the soil may provide an indication of a moisture level.

Referring back to the updated traversability difficulty, the control system may compare the previously determined traversability difficulty with the newly determined updated traversability difficulty. If the difference between the traversability difficulty and the updated traversability difficulty is greater than a threshold, this may indicate that the previously determined traversability difficulty was inaccurate. To account for this, the farming machine may perform a second farming action. Similar to the actions described with reference to step 540, the second action may be performed to prevent (or reduce the likelihood of) the farming machine attempting to traverse an untraversable field portion. The second action can include any of the actions described with reference to step 540.

IV.B Applying the Moisture Model

FIG. 7 illustrates another method for operating in a field with moisture by a farming machine (e.g., machine 100), in accordance with one or more embodiments. The method 700 may be performed from the perspective of the control system 130. The method 700 can include greater or fewer steps than described herein. Additionally, the steps can be performed in different order, or by different components than described herein.

Similar to step 510, a farming machine moves 710 along a route in a field with moisture.

The control system identifies 720 a farming action to perform by the farming machine at a portion of the field. The control system may identify the farming action in response to analyzing an image from an image sensor (e.g., sensor 210) or analyzing diagnostic information from sensors of the farming machine. The control system may also identify the farming action based on instructions from an operator. For example, an operator may instruct the farming machine to apply a treatment to a crop in the field. Thus, in either case, the farming machine may identify the treatment action in response to identifying a crop in the field. The control system typically identifies the farming action prior to the farming machine moving through the field portion, but it may identify the action as the farming machine is moving through the field portion.

In the context of step 720, a farming action is an action the farming machine may perform while in the portion of the field (e.g., while moving through the field portion). Examples of farming actions include performing a treatment action, modifying a treatment parameter, modifying an operational parameter, and modifying a sensor parameter. The identified farming action may be a farming action described with reference step 540.

The control system determines 730 a measure of moisture (also referred to as the moisture level) for a portion of the field by applying a moisture model to an image of the portion of the field.

As described with reference to step 520, the image of the portion of the field includes a group of pixels that indicate a measure of moisture of the field portion. One or more image sensors may capture the image. Example image sensors that can capture the image are described with reference to the detection mechanism 110. The image sensors may be coupled to the farming machine and oriented to capture the portion of the field.

The moisture model may be independent of the traversability model. As described with reference to step 530, the moisture model may determine the measure of moisture by analyzing one or more groups of pixels in the image. For example, visual properties such as texture, reflection, and saturation indicate the presence, location, and amount of moisture. In addition to analyzing pixels of the image, the traversability model may receive non-visual information to determine the moisture level of the portion of the field, such as temperature, humidity, wind, weather data, topography, and soil maps.

The control system determines 740 a likelihood that the farming machine performing the identified farming action will damage the portion of the field based on the identified action and the determined measure of moisture for the portion of the field.

The likelihood that the farming machine performing the identified farming action will damage the portion of the field may refer to a specific type of damage and/or an amount of damage. An operator of the farming machine may specify the type and amount or they may be predetermined. For example, an operator specifies that they can tolerate an action damaging (or killing) a few plants but do not want an action to damage (or kill) a threshold number of plants. Damage to a plant may be caused by the farming machine running it over, a component of the farming machine hitting it, or mud thrown by the farming machine hitting it. Determining whether a farming action will damage a plant may be based on the type of plant, a growth stage, a size, a location, and/or a planting configuration of the plant. Referring back to specifying the type and amount of damage, in another example, an operator specifies that they can tolerate an action slightly modifying the field but do not want an action to form a new water run-off channel in the field. Additional example types of damage to a portion of the field include damaging a threshold number of rows in the field, changing an irrigation pathway above a threshold amount, enlarging a preexisting water run-off channel above a threshold amount, enlarging a local depression above a threshold amount (this may increase the size of a body in the future), changing the gradient of the field portion above a threshold amount, and compacting the soil above a threshold amount. Another form of damage is unwanted biological consequences stemming from a farming action being performed in the presence of moisture. For example, planting into wet soil may be undesirable. Or applications of certain herbicides may be more/less effective if the crop is wet. In another example, field modifications from ruts can reduce or impact the ability to harvest a crop later.

The control system may use a damage model to determine the likelihood. Generally, a higher level of moisture at the field portion results in a higher likelihood that an action will damage the field portion (and vice versa), however the relationship depends on the action, may not be linear, and may be based on other factors, some of which are further described below. For example, the damage model is a weighted model with a weight for each factor, where each weight indicates, for the determined measure of moisture, how strongly its corresponding factor affects the likelihood. In some embodiments, the relationship between the moisture level, the farming action, and the likelihood is machine learned, for example historical farming action data. Historical farming action data may include farming actions performed at field portions, measures of moisture of the field portions, and damage (if any) that the actions caused to the field portions. Other factors that may affect the likelihood determination include:

(1) The route of the farming machine. The direction of travel through the field portion may affect whether the action damages the field portion. For example, a farming machine performing an action while moving uphill may be more likely to damage the field portion than the farming machine performing the action while moving downhill. In another example, the direction of travel relative to rows in the field or a body of moisture determines whether the action damages the field portion.

(2) Soil type of the field portion. A soil type may affect how the soil responds to the farming action.

(3) The gradient of the field portion. Generally, a higher gradient (e.g., regardless of the route) increases the likelihood the action will damage the field portion while a smaller gradient decreases the likelihood. To determine the gradient, the control system may identify local minimums or maximums in the field portion.

(4) Operational parameters. For example, a farming machine with a higher speed may increase the likelihood of the action damaging the field portion. If the damage model determines the likelihood prior to the farming machine moving through the field portion, the damage model may assume that the operational parameters will remain constant (or within a threshold range) while the farming machine moves through the field portion.

(5) Characteristics of the farming machine. For example, a heavy farming machine may have a high likelihood of compacting the soil and enlarging depressions in the field. Examples characteristics, such as wheel type, wheel size, etc., are described with reference to step 540.

In some cases, the likelihood is based on the farming machine performing the identified action in the field portion. These cases may occur if the likelihood of damaging the field is small or if the amount of potential damage is small. In these embodiments, the control system may determine whether the action being performed is damaging the field.

For example, the control system analyzes images of the farming machine performing the action.

If the likelihood does not exceed a threshold likelihood (e.g., provided by an operator or predetermined), the farming action may perform the identified action, for example, when the farming machine enters the field portion. However, if the likelihood exceeds the threshold likelihood, the control system performs 750 a second farming action, where the likelihood that the farming machine performing the second farming action will damage the portion of the field is less than the threshold likelihood.

A farming action in the context of step 750 is an action performed by the farming machine and intended to prevent or reduce the likelihood of the farming machine damaging the portion of field. The second action may be one or more of the actions described with reference to step 720, however the second action is either a different action or a same action that is performed with different parameters (e.g., the second action has a different type of spray or different tilling depth) than the identified action in step 720. Depending on the situation, the second farming action may be performed instead of the identified farming action or the second farming action may modify the identified action (e.g., to reduce the likelihood that the identified action will damage the field). In another example, the second farming action nullifies the identified farming action such that the identified farming action is not performed (or no longer performed) by the farming machine. For example, if the control system determines that moisture (e.g., a puddle) will spread a spray treatment applied to a plant (e.g., weed) to another plant (e.g., a crop), the second farming action may cancel the spray treatment action being performed by the farming machine.

As stated above, the control system may determine the measure of moisture and the likelihoods of the first and second actions while the farming machine is moving towards or through the portion of the field. However, the control system may determine one or more of these values prior to this. For example, the control system applies the moisture model to the image of the field portion (e.g., using cloud processing) prior to the farming machine moving through the field. When it is time to move in the field (e.g., later in the day or on another day), farming action instructions may be provided to the farming machine. Said differently, the measure of moisture and the likelihoods of the first and second actions may be determined at a first time and the farming machine may perform the second farming action at a second time, where the second time can occur at any time after the first time.

In some embodiments, as the farming machine gets closer to the field portion or travels through the field portion, it determines an updated likelihood of the identified action damaging the portion of the field. If the updated likelihood is below the threshold likelihood, the farming machine may perform the identified action.

Methods 500 and 700 may be performed independently. In some embodiments, the methods are interconnected. For example, the farming action in step 540 may be the identified action in step 720.

IV.C Implementation of Moisture Model

There are several methods to determine a measure of moisture in a captured image. One method of determining moisture information from a captured image is a moisture model that operates on a convex hull optimization model. Another method of determining moisture information from a captured image is a moisture model that operates on a fully convolutional encoder-decoder network. For example, the moisture model can be implemented as functions in a neural network trained to determine moisture information from visual information encoded as pixels in an image. The moisture model may function similarly to a pixelwise semantic segmentation model where the classes for labelling bodies of moisture indicate measures of moisture.

Figure 8:
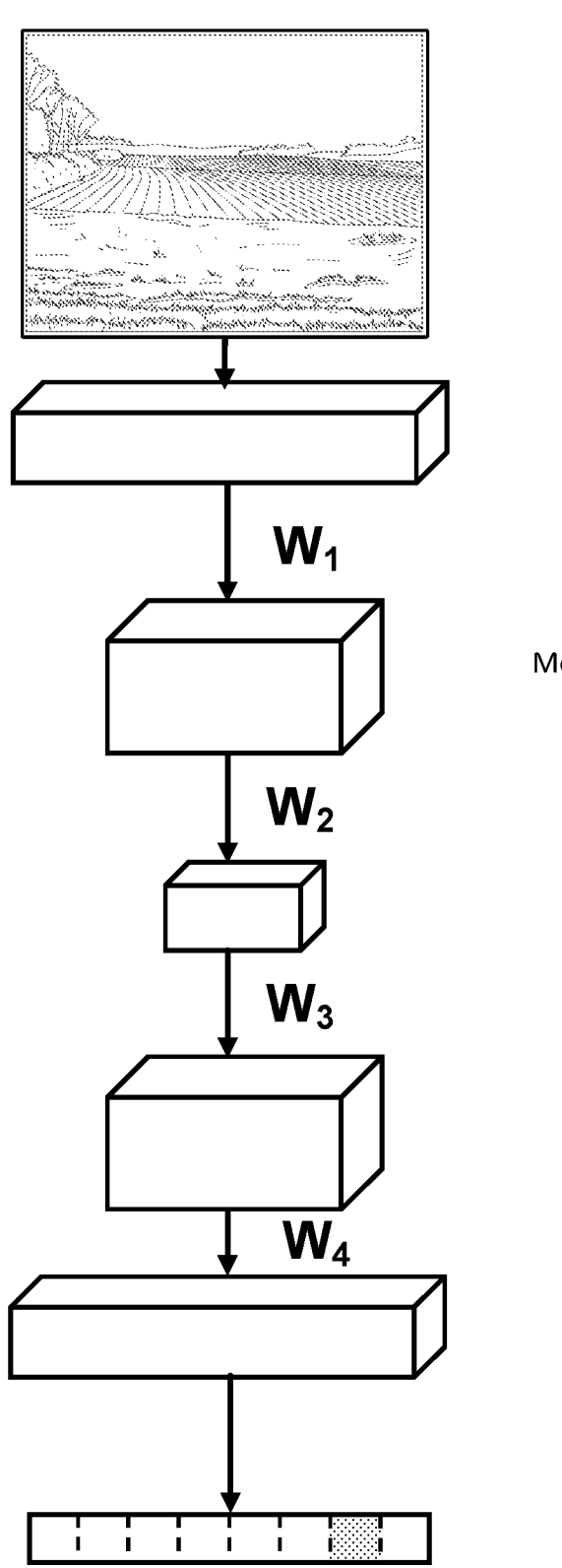
FIG. 8 illustrates a representation of a moisture model, in accordance with an example embodiment.

Herein, the encoder-decoder network may be implemented by a control system 130 as a moisture model 805. The control system 130 can execute the moisture model 805 to identify moisture associated with pixels in an accessed image 800 and quickly generate an accurate measure of moisture 860. To illustrate, FIG. 8 is a representation of a moisture model, in accordance with one example embodiment.

In the illustrated embodiment, the moisture model 805 is a convolutional neural network model with layers of nodes, in which values at nodes of a current layer are a transformation of values at nodes of a previous layer. A transformation in the model 805 is determined through a set of weights and parameters connecting the current layer and the previous layer. For example, as shown in FIG. 8, the example model 805 includes five layers of nodes: layers 810, 820, 830, 840, and 850. The control system 130 applies the function $W_1$ to transform from layer 810 to layer 820, applies the function $W_2$ to transform from layer 820 to layer 830, applies the function $W_3$ to transform from layer 830 to layer 840, and applies the function $W_4$ to transform from layer 840 to layer 850. In some examples, the transformation can also be determined through a set of weights and parameters used to transform between previous layers in the model. For example, the transformation $W_4$ from layer 840 to layer 850 can be based on parameters used to accomplish the transformation $W_1$ from layer 810 to 820.

In an example process, the control system 130 inputs an accessed image 800 (e.g., the image in FIG. 6E) to the model 805 and encodes the image onto the convolutional layer 810. After processing by the control system 130, the model 805 outputs a measure of moisture 860 decoded from the output layer 850. In the identification layer 830, the control system 130 employs the model 805 to identify moisture information associated with pixels in the accessed image 800. The moisture information may be indicative of amounts of moisture at a portion of the field and their locations in the accessed image 800. The control system 130 reduces the dimensionality of the convolutional layer 810 to that of the identification layer 830 to identify moisture information in the accessed image pixels, and then increases the dimensionality of the identification layer 830 to generate a measure of moisture 860. In some examples, the moisture model 805 can group pixels in an accessed image 800 based on moisture information identified in the identification layer 830 when generating the measure of moisture 860.

As previously described, the control system 130 encodes an accessed image 800 to a convolutional layer 810. In one example, a captured image is directly encoded to the convolutional layer 810 because the dimensionality of the convolutional layer 810 is the same as a pixel dimensionality (e.g., number of pixels) of the accessed image 800. In other examples, the captured image can be adjusted such that the pixel dimensionality of the captured image is the same as the dimensionality of the convolutional layer 810. For example, the accessed image 800 may be cropped, reduced, scaled, etc.

The control system 130 applies the model 805 to relate an accessed image 800 in the convolutional layer 810 to moisture information in the identification layer 830. The control system 130 retrieves relevant information between these elements by applying a set of transformations (e.g., $W_1$, $W_2$, etc.) between the corresponding layers. Continuing with the example from FIG. 8, the convolutional layer 810 of the model 805 represents an accessed image 800, and identification layer 830 of the model 805 represents moisture information encoded in the image. The control system 130 identifies moisture information corresponding to pixels in an accessed image 800 by applying the transformations $W_1$ and $W_2$ to the pixel values of the accessed image 800 in the space of convolutional layer 810. The weights and parameters for the transformations may indicate relationships between the visual information contained in the accessed image and the inherent moisture information encoded in the accessed image 800. For example, the weights and parameters can be a quantization of shapes, distances, obscuration, etc. associated with moisture information in an accessed image 800. The control system 130 may learn the weights and parameters using historical user interaction data and labelled images.

In the identification layer 830, the control system maps pixels in the image to associated moisture information based on the latent information about the objects represented by the visual information in the captured image. The identified moisture information can be used to generate a measure of moisture 860. To generate a measure of moisture 860, the control system 130 employs the model 805 and applies the transformations $W_3$ and $W_4$ to the moisture information identified in identification layer 830. The transformations result in a set of nodes in the output layer 850. The weights and parameters for the transformations may indicate relationships between the image pixels in the accessed image 800 and a measure of moisture 860. In some cases, the control system 130 directly outputs a measure of moisture 860 from the nodes of the output layer 850, while in other cases the control system 130 decodes the nodes of the output layer 850 into a measure of moisture 860. That is, model 805 can include a conversion layer (not illustrated) that converts the output layer 850 to a measure of moisture 860.

The weights and parameters for the moisture model 805 can be collected and trained, for example, using data collected from previously captured visual images and a labeling process. The labeling process increases the accuracy and reduces the amount of time required by the control system 130 employing the model 805 to identify moisture information associated with pixels in an image.

Additionally, the model 805 can include layers known as intermediate layers. Intermediate layers are those that do not correspond to convolutional layer 110 for the accessed image 800, the identification layer 830 for the moisture information, and an output layer 850 for the measure of moisture 860. For example, as shown in FIG. 8, layers 820 are intermediate encoder layers between the convolutional layer 810 and the identification layer 830. Layer 840 is an intermediate decoder layer between the identification layer 830 and the output layer 850. Hidden layers are latent representations of different aspects of an accessed image that are not observed in the data but may govern the relationships between the elements of an image when identifying a measure of moisture associated with pixels in an image. For example, a node in the hidden layer may have strong connections (e.g., large weight values) to input values and values of nodes in an identification layer that share the commonality of moisture information. Specifically, in the example model of FIG. 8, nodes of the hidden layers 820 and 840 can link inherent visual information in the accessed image 800 that share common characteristics to help determine moisture information for one or more pixels.

Additionally, each intermediate layer may be a combination of functions such as, for example, residual blocks, convolutional layers, pooling operations, skip connections, concatenations, etc. Any number of intermediate encoder layers 820 can function to reduce the convolutional layer to the identification layer and any number of intermediate decoder layers 840 can function to increase the identification layer 830 to the output layer 850. Alternatively stated, the encoder intermediate layers reduce the pixel dimensionality to the moisture identification dimensionality, and the decoder intermediate layers increase the identification dimensionality to the measure of moisture dimensionality.

Furthermore, in various embodiments, the functions of the model 805 can reduce the accessed image 800 and identify any number of objects in a field. The identified objects are represented in the identification layer 830 as a data structure having the identification dimensionality. In various other embodiments, the identification layer can identify latent information representing other objects in the accessed image. For example, the identification layer 830 can identify a result of a plant treatment, soil, an obstruction, or any other object in the field.

Other models described herein, such as the traversability model and the damage model, may also be encoder-decoder networks similar to the moisture model 805 illustrated in FIG. 8. That is, an encoder-decoder network may be used to extract a traversability difficulty of a field portion, or an expected damage of a action for the field portion. In some cases, one encoder can be used for multiple decoders. For example, a single image can be encoded onto a convolutional neural network and the traversability, moisture, and damage expectations may be extracted from that image.

IV.D Training a Moisture Model

The control system 130 or another entity may train the moisture model (e.g., moisture model 334). For example, the moisture model is trained using a plurality of the labelled images of one or more field portions. The labels in the images may indicate pixels with moisture information. The labels may be designated by an operator or labeled by someone offsite. In addition to labeling an image, non-visual information, such as temperature, humidity, wind, weather data (e.g., historical rainfall), topography, and a soil map, may be associated with the labeled images and used by the control system 130 to train the moisture model.

As described above, training the moisture model generates functions that are able to identify latent information in an image that corresponds to moisture information. The control system 130 may train the moisture model using the labelled images such that the moisture model tags a captured image with one or more measures of moisture. This approach allows the farming machine to determine a measure of moisture for a field portion.

The control system 130 can train the moisture model periodically during operation of the farming machine, at a determined time, or before the moisture model is implemented on a farming machine. Additionally, the moisture model can be trained by another system such that the moisture model can be implemented on a control system of a farming machine as a standalone model. Notably, in some examples, the aspect of the control system 130 that trains the moisture model may not be collocated on the farming machine. That is, the moisture model may be trained on a machine separate from the farming machine 100 and transferred to the farming machine.

Other models described herein, such as the traversability model and the damage model, may also be trained similar to the moisture model. That is, a labeling process may be used to train the traversability model or the damage model. For example, the traversability model is trained using images that are labelled with moisture information and additional factor information, such as soil information, gradient information, and a depth of track marks in the images.

V. Control System

Figure 9:
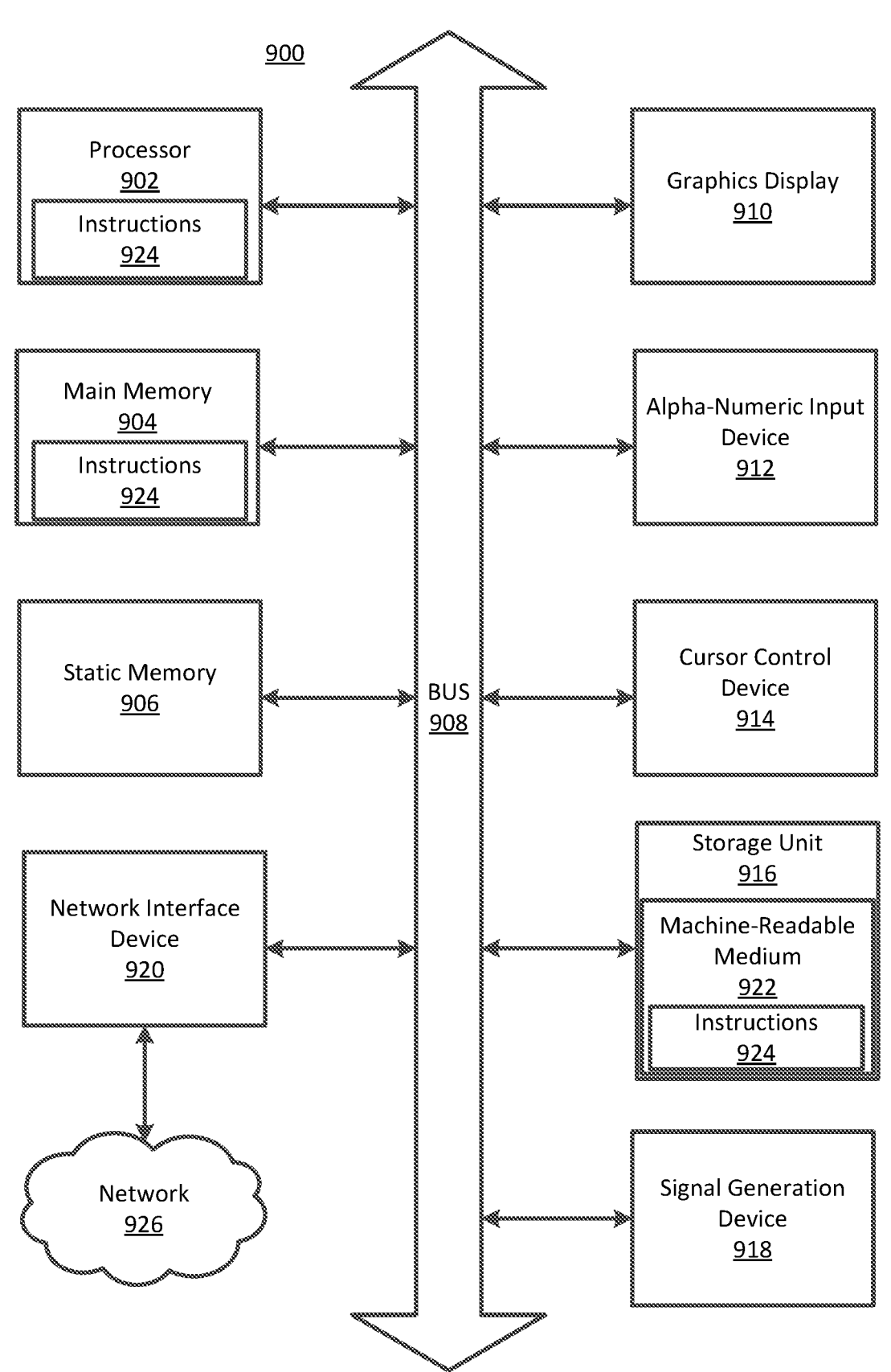
FIG. 9 illustrates a schematic of a control system, in accordance with an example embodiment.

FIG. 9 is a block diagram illustrating components of an example machine for reading and executing instructions from a machine-readable medium. Specifically, FIG. 9 shows a diagrammatic representation of control system 130 in the example form of a computer system 900. The computer system 900 can be used to execute instructions 924 (e.g., program code or software) for causing the machine to perform any one or more of the methodologies (or processes) described herein. In alternative embodiments, the machine operates as a standalone device or a connected (e.g., networked) device that connects to other machines. In a networked deployment, the machine may operate in the capacity of a server machine or a client machine in a server-client network environment, or as a peer machine in a peer-to-peer (or distributed) network environment.

The machine may be a server computer, a client computer, a personal computer (PC), a tablet PC, a set-top box (STB), a smartphone, an internet of things (IoT) appliance, a network router, switch or bridge, or any machine capable of executing instructions 924 (sequential or otherwise) that specify actions to be taken by that machine. Further, while only a single machine is illustrated, the term "machine" shall also be taken to include any collection of machines that individually or jointly execute instructions 924 to perform any one or more of the methodologies discussed herein.

The example computer system 900 includes one or more processing units (generally processor 902). The processor 902 is, for example, a central processing unit (CPU), a graphics processing unit (GPU), a digital signal processor (DSP), a control system, a state machine, one or more application specific integrated circuits (ASICs), one or more radio-frequency integrated circuits (RFICs), or any combination of these. The computer system 900 also includes a main memory 904. The computer system may include a storage unit 916. The processor 902, memory 904, and the storage unit 916 communicate via a bus 908.

In addition, the computer system 900 can include a static memory 906, a graphics display 910 (e.g., to drive a plasma display panel (PDP), a liquid crystal display (LCD), or a projector). The computer system 900 may also include alphanumeric input device 912 (e.g., a keyboard), a cursor control device 914 (e.g., a mouse, a trackball, a joystick, a motion sensor, or other pointing instrument), a signal generation device 918 (e.g., a speaker), and a network interface device 920, which also are configured to communicate via the bus 908.

The storage unit 916 includes a machine-readable medium 922 on which is stored instructions 924 (e.g., software) embodying any one or more of the methodologies or functions described herein. For example, the instructions 924 may include the functionalities of modules of the system 130 described in FIG. 2. The instructions 924 may also reside, completely or at least partially, within the main memory 904 or within the processor 902 (e.g., within a processor's cache memory) during execution thereof by the computer system 900, the main memory 904 and the processor 902 also constituting machine-readable media. The instructions 924 may be transmitted or received over a network 926 via the network interface device 920.

VI. Additional Considerations

In the description above, for purposes of explanation, numerous specific details are set forth in order to provide a thorough understanding of the illustrated system and its operations. It will be apparent, however, to one skilled in the art that the system can be operated without these specific details. In other instances, structures and devices are shown in block diagram form in order to avoid obscuring the system.

Reference in the specification to "one embodiment" or "an embodiment" means that a particular feature, structure, or characteristic described in connection with the embodiment is included in at least one embodiment of the system. The appearances of the phrase "in one embodiment" in various places in the specification are not necessarily all referring to the same embodiment.

Some portions of the detailed descriptions are presented in terms of algorithms or models and symbolic representations of operations on data bits within a computer memory. An algorithm is here, and generally, conceived to be steps leading to a desired result. The steps are those requiring physical transformations or manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Some of the operations described herein are performed by a computer physically mounted within a machine. This computer may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of non-transitory computer readable storage medium suitable for storing electronic instructions.

The figures and the description above relate to various embodiments by way of illustration only. It should be noted that from the following discussion, alternative embodiments of the structures and methods disclosed herein will be readily recognized as viable alternatives that may be employed without departing from the principles of what is claimed.

One or more embodiments have been described above, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct physical or electrical contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article or apparatus that comprises a list of elements is not necessarily limited to only those elements but may include other elements not expressly listed or inherent to such process, method, article or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B is true (or present).

In addition, use of the "a" or "an" are employed to describe elements and components of the embodiments herein. This is done merely for convenience and to give a general sense of the system. This description should be read to include one or at least one and the singular also includes the plural unless it is obvious that it is meant otherwise.

Upon reading this disclosure, those of skill in the art will appreciate still additional alternative structural and functional designs for a system and a process for identifying and treating plants with a farming machine including a control system executing a semantic segmentation model. Thus, while particular embodiments and applications have been illustrated and described, it is to be understood that the disclosed embodiments are not limited to the precise construction and components disclosed herein. Various modifications, changes and variations, which will be apparent to those, skilled in the art, may be made in the arrangement, operation and details of the method and apparatus disclosed herein without departing from the spirit and scope defined in the appended claims.

What is claimed is:

1. A method for operating in a field with moisture by a farming machine with a wheel or track and a treatment mechanism configured to perform treatment actions to one or more plants in the field, the method comprising:

moving, by the farming machine, along a route in the field by the wheel or track;

identifying a first farming action to perform by the farming machine at a portion of the field, the identified first farming action to be performed as the farming machine moves through the portion along the route;

determining, by applying a traversability model to an image of the wheel or track of the farming machine, a traversability difficulty value for the portion of the field, the traversability model configured to:

determine, based on the image, a mud buildup on the wheel or track;

determine a measure of moisture for the portion of the field based on the determined mud buildup; and determine the traversability difficulty value based on the measure of moisture;

determining a traversability capability value of the farming machine;

determining whether the traversability difficulty value is above the traversability capability value of the farming machine, in response to the traversability difficulty value being above the traversability capability value of the farming machine, determining a second farming action for a next portion of the field, the second farming action modifying the first farming action; and performing the second farming action in the field.

2. The method of claim 1, wherein the second farming action is performed instead of the first farming action.

3. The method of claim 1, wherein the second farming action comprises nullifying the first farming action such that the first farming action is not performed as the farming machine moves along the route.

4. The method of claim 1, wherein the second farming action includes at least one of: modifying the route or modifying a driving parameter of the farming machine.

5. The method of claim 1, wherein determining the measure of moisture is further based on diagnostic information from one or more sensors of the farming machine.

6. The method of claim 1, wherein determining the traversability capability value of the farming machine is based on characteristics describing the farming machine, the characteristics including at least one of: a wheel type, a wheel size, a tread type, an engine/motor type, a drive type, a make, a model, a weight, a fuel level, the treatment mechanism, and/or a coupling mechanism of the farming machine.

7. The method of claim 1, wherein determining the traversability difficulty value is further based on one or more types of soil in the portion of the field and a gradient of the portion of the field.

8. The method of claim 1, wherein the farming machine is autonomous.

9. The method of claim 1, wherein the traversability model is a weighted model.

10. A farming machine comprising a wheel or track and a treatment mechanism configured to perform treatment actions to one or more plants in a field, the farming machine configured to:

move along a route in the field by the wheel or track;

identify a first farming action to perform at a portion of the field, the identified first farming action to be performed as the farming machine moves through the portion along the route;

determine, by applying a traversability model to an image of the wheel or track of the farming machine, a traversability difficulty value for the portion of the field, the traversability model configured to;

determine, based on the image, a mud buildup on the wheel or track;

determine a measure of moisture for the portion of the field based on the determined mud buildup; and determine the traversability difficulty value based on the measure of moisture;

determine a traversability capability value of the farming machine;

determine whether the traversability difficulty value is above the traversability capability value of the farming machine, in response to the traversability difficulty value being above the traversability capability value of the farming machine, determining a second farming action for a next portion of the field, the second farming action modifying the first farming action; and perform the second farming action in the field.

11. The farming machine of claim 10, wherein the second farming action is performed instead of the first farming action.

12. The farming machine of claim 10, wherein the second farming action comprises nullifying the first farming action such that the first farming action is not performed as the farming machine moves along the route.

13. The farming machine of claim 10, wherein the second farming action includes at least one of: modifying the route or modifying a driving parameter of the farming machine.

14. The farming machine of claim 10, wherein determining the traversability difficulty value is further based on diagnostic information from one or more sensors of the farming machine.

15. The farming machine of claim 10, wherein determining the traversability capability value of the farming machine is based on characteristics describing the farming machine, the characteristics including at least one of: a wheel type, a wheel size, a tread type, an engine/motor type, a drive type, a make, a model, a weight, a fuel level, the treatment mechanism, and/or a coupling mechanism of the farming machine.

16. The farming machine of claim 10, wherein determining the traversability difficulty value is further based on one or more types of soil in the portion of the field and a gradient of the portion of the field.

17. One or more non-transitory computer-readable storage mediums storing instructions that, when executed by a set of one or more processors, causes the set of one or more processors to:

cause a farming machine to move along a route in a field, the farming machine comprising a wheel or track and a treatment mechanism configured to perform treatment actions to one or more plants in the field;

identify a first farming action to perform at a portion of the field, the identified first farming action to be performed as the farming machine moves through the portion along the route;

determine, by applying a traversability model to an image of the wheel or track of the farming machine, a traversability difficulty value for the portion of the field, the traversability model configured to:

determine, based on the image, a mud buildup on the wheel or track;

determine a measure of moisture for the portion of the field based on the determined mud buildup; and determine the traversability difficulty value based on the measure of moisture;

determine a traversability capability value of the farming machine;

determine whether the traversability difficulty value is above the traversability capability value of the farming machine, in response to the traversability difficulty value being above the traversability capability value of the farming machine, determine a second farming action for a next portion of the field, the second farming action modifying the first farming action; and perform the second farming action in the field.

\* \* \* \* \*